(12) United States Patent
Khachaturian

(10) Patent No.: US 11,504,014 B2
(45) Date of Patent: Nov. 22, 2022

(54) APPARATUS AND METHODS FOR MEASURING BLOOD PRESSURE AND OTHER VITAL SIGNS VIA A FINGER

(71) Applicant: Arc Devices Limited, Dublin (IE)

(72) Inventor: Mark Haig Khachaturian, Palm Beach Gardens, FL (US)

(73) Assignee: ARC DEVICES LIMITED, Dublin (IE)

( * ) Notice: Subject to any disclaimer, the term of this patent is extended or adjusted under 35 U.S.C. 154(b) by 0 days.

(21) Appl. No.: 17/330,887

(22) Filed: May 26, 2021

(65) Prior Publication Data

US 2021/0369126 A1    Dec. 2, 2021

Related U.S. Application Data

(60) Provisional application No. 63/033,006, filed on Jun. 1, 2020.

(51) Int. Cl.
| | | |
|---|---|---|
| *A61B 5/022* | (2006.01) | |
| *A61B 5/0205* | (2006.01) | |
| *A61B 5/00* | (2006.01) | |
| *A61B 5/024* | (2006.01) | |

(52) U.S. Cl.
CPC ........ *A61B 5/02241* (2013.01); *A61B 5/0205* (2013.01); *A61B 5/02225* (2013.01); *A61B 5/0059* (2013.01); *A61B 5/024* (2013.01); *A61B 5/742* (2013.01)

(58) Field of Classification Search
CPC .............. A61B 5/02241; A61B 5/0205; A61B 5/02225; A61B 5/0059; A61B 5/024; A61B 5/742
See application file for complete search history.

(56) References Cited

U.S. PATENT DOCUMENTS

| | | |
|---|---|---|
| 4,315,150 A | 2/1982 | Darringer et al. |
| 4,322,012 A | 3/1982 | Conti |
| 4,394,773 A | 7/1983 | Ruell |
| (Continued) | | |

FOREIGN PATENT DOCUMENTS

| | | |
|---|---|---|
| CA | 2160252 | 10/1994 |
| CN | 1271562 A | 11/2000 |
| (Continued) | | |

OTHER PUBLICATIONS

Unknown, "Crit-Line III Monitor", Fresenius Medical Care, retrieved Nov. 17, 2021 from https://fmcna.com/products/fluid-management/crit-line-iii/, 5 pages.

(Continued)

*Primary Examiner* — Lynsey C Eiseman
*Assistant Examiner* — Jessandra F Hough
(74) *Attorney, Agent, or Firm* — Steven J. Rocci P.C.

(57) ABSTRACT

There is disclosed a vital sign measuring device (VSMD) for obtaining an indication of a person's blood pressure via the person's finger by means of a finger cuff having an inflatable bladder. Blood pressure may be determined without the use of any electromagnetic radiation, such as miniature dynamic light sensing (mDLS). Apparatuses and methods for obtaining an indication of other vital signs, including hematocrit and total protein, are also disclosed.

1 Claim, 27 Drawing Sheets

(56) References Cited

U.S. PATENT DOCUMENTS

| | | | |
|---|---|---|---|
| 4,602,642 A | 7/1986 | O'Hara et al. | |
| 4,634,294 A | 1/1987 | Christol et al. | |
| 4,709,690 A | 12/1987 | Haber | |
| 4,797,840 A | 1/1989 | Fraden | |
| 5,017,018 A | 5/1991 | Iuchi et al. | |
| 5,067,162 A | 11/1991 | Driscoll, Jr. et al. | |
| 5,077,476 A | 12/1991 | Rosenthal | |
| 5,133,605 A | 7/1992 | Nakamura | |
| 5,150,969 A | 9/1992 | Goldberg et al. | |
| 5,272,340 A | 12/1993 | Anbar | |
| 5,325,442 A | 6/1994 | Knapp | |
| 5,351,303 A | 9/1994 | Willmore | |
| 5,368,038 A | 11/1994 | Fraden | |
| 5,398,681 A | 3/1995 | Kupershmidt | |
| 5,404,879 A * | 4/1995 | Frankenreiter | A61B 5/022 600/494 |
| 5,499,627 A | 3/1996 | Steuer et al. | |
| 5,689,576 A | 11/1997 | Schneider et al. | |
| 5,737,439 A | 4/1998 | Lapsley et al. | |
| 5,743,644 A | 4/1998 | Kobayashi | |
| 5,909,501 A | 6/1999 | Thebaud | |
| 5,940,526 A | 8/1999 | Setlak et al. | |
| 5,953,441 A | 9/1999 | Setlak | |
| 6,001,066 A | 12/1999 | Canfield et al. | |
| 6,095,682 A | 8/2000 | Hollander et al. | |
| 6,118,890 A | 9/2000 | Senior | |
| 6,134,340 A | 10/2000 | Hsu et al. | |
| 6,241,288 B1 | 6/2001 | Bergenek et al. | |
| 6,266,546 B1 | 7/2001 | Steuer et al. | |
| 6,286,994 B1 | 9/2001 | Boesel et al. | |
| 6,289,114 B1 | 9/2001 | Mainguet | |
| 6,292,685 B1 | 9/2001 | Pompei | |
| 6,327,376 B1 | 12/2001 | Harkin | |
| 6,343,141 B1 | 1/2002 | Okada et al. | |
| 6,358,216 B1 | 3/2002 | Kraus et al. | |
| 6,445,938 B1 | 9/2002 | Berman et al. | |
| 6,483,929 B1 | 11/2002 | Murakami et al. | |
| 6,505,059 B1 | 1/2003 | Kollias et al. | |
| 6,546,122 B1 | 4/2003 | Russo | |
| 6,560,352 B2 | 5/2003 | Rowe et al. | |
| 6,587,701 B1 | 7/2003 | Strane et al. | |
| 6,728,560 B2 | 4/2004 | Kollias et al. | |
| 6,742,927 B2 | 6/2004 | Bellifemine | |
| 6,751,342 B2 | 6/2004 | Shepard | |
| 6,757,412 B1 | 6/2004 | Parsons | |
| 6,819,950 B2 | 11/2004 | Mills | |
| 6,832,000 B2 | 12/2004 | Herman et al. | |
| 7,092,376 B2 | 8/2006 | Schuman | |
| 7,138,905 B2 | 11/2006 | Pavlidis et al. | |
| 7,140,768 B2 | 11/2006 | Prabhakar | |
| 7,214,953 B2 | 5/2007 | Setlak et al. | |
| 7,321,701 B2 | 1/2008 | Setlak et al. | |
| 7,335,163 B2 | 2/2008 | Lam et al. | |
| 7,339,685 B2 | 3/2008 | Carlson et al. | |
| 7,346,386 B2 | 3/2008 | Pompei | |
| 7,351,974 B2 | 4/2008 | Setlak | |
| 7,358,514 B2 | 4/2008 | Setlak et al. | |
| 7,358,515 B2 | 4/2008 | Setlak et al. | |
| 7,361,919 B2 | 4/2008 | Setlak | |
| 7,433,729 B2 | 10/2008 | Setlak et al. | |
| 7,520,668 B2 | 4/2009 | Chen | |
| 7,572,056 B2 | 8/2009 | Lane | |
| 7,601,123 B2 | 10/2009 | Tweed et al. | |
| 7,671,351 B2 | 3/2010 | Setlak et al. | |
| 7,787,938 B2 | 8/2010 | Pompei | |
| 7,915,601 B2 | 3/2011 | Setlak et al. | |
| 8,194,942 B2 | 6/2012 | Tobe et al. | |
| 8,213,689 B2 | 7/2012 | Yagnik et al. | |
| 8,249,547 B1 | 8/2012 | Fellner | |
| 8,401,285 B1 | 3/2013 | Rezaee et al. | |
| 8,452,382 B1 | 5/2013 | Roth | |
| 8,493,482 B2 | 7/2013 | Cote et al. | |
| 8,517,603 B2 | 8/2013 | Fraden | |
| 8,527,038 B2 | 9/2013 | Moon et al. | |
| 8,617,081 B2 | 12/2013 | Mestha et al. | |
| 8,693,739 B2 | 4/2014 | Weng et al. | |
| 8,814,800 B2 | 8/2014 | Fortin et al. | |
| 8,849,379 B2 | 9/2014 | Abreu | |
| 9,008,458 B2 | 4/2015 | Pack | |
| 9,321,394 B2 | 4/2016 | Bouffay et al. | |
| 9,433,360 B2 | 9/2016 | Lam et al. | |
| 9,442,065 B2 | 9/2016 | Gulati et al. | |
| 9,497,534 B2 | 11/2016 | Prest et al. | |
| 10,039,500 B2 | 8/2018 | Newberry | |
| 10,485,431 B1 | 11/2019 | Khachaturian et al. | |
| 10,492,684 B2 | 12/2019 | Khachaturian et al. | |
| 10,506,926 B2 | 12/2019 | Khachaturian et al. | |
| 2001/0005424 A1 | 6/2001 | Marksteiner | |
| 2002/0067845 A1 | 6/2002 | Griffis | |
| 2002/0076089 A1 | 6/2002 | Muramatsu et al. | |
| 2002/0077850 A1 | 6/2002 | McMenimen et al. | |
| 2002/0138768 A1 | 9/2002 | Murakami et al. | |
| 2002/0143257 A1 | 10/2002 | Newman et al. | |
| 2002/0172410 A1 | 11/2002 | Shepard | |
| 2003/0069486 A1 | 4/2003 | Sueppel et al. | |
| 2003/0069487 A1 | 4/2003 | Mortara | |
| 2003/0078622 A1 | 4/2003 | Cansell et al. | |
| 2003/0123714 A1 | 7/2003 | O'Gorman et al. | |
| 2003/0126448 A1 | 7/2003 | Russo | |
| 2003/0169910 A1 | 9/2003 | Reisman et al. | |
| 2003/0190062 A1 | 10/2003 | Noro et al. | |
| 2004/0013162 A1 | 1/2004 | Beerwerth | |
| 2004/0019293 A1 | 1/2004 | Schweitzer et al. | |
| 2004/0097818 A1 | 5/2004 | Schmid et al. | |
| 2004/0116822 A1 | 6/2004 | Lindsey | |
| 2004/0120383 A1 | 6/2004 | Kennedy et al. | |
| 2004/0153341 A1 | 8/2004 | Brandt et al. | |
| 2004/0186357 A1 | 9/2004 | Soderberg et al. | |
| 2004/0193068 A1 | 9/2004 | Burton et al. | |
| 2005/0023991 A1 | 2/2005 | Kemper | |
| 2005/0054908 A1 | 3/2005 | Blank et al. | |
| 2005/0203350 A1 | 9/2005 | Beck | |
| 2005/0206518 A1 | 9/2005 | Welch et al. | |
| 2005/0209515 A1 | 9/2005 | Hockersmith et al. | |
| 2005/0288571 A1 | 12/2005 | Perkins et al. | |
| 2006/0004271 A1 | 1/2006 | Peyser et al. | |
| 2006/0030759 A1 | 2/2006 | Weiner et al. | |
| 2006/0045316 A1 | 3/2006 | Hauke et al. | |
| 2006/0110015 A1 | 5/2006 | Rowe | |
| 2006/0155589 A1 | 7/2006 | Lane et al. | |
| 2006/0195024 A1 | 8/2006 | Benni | |
| 2006/0209631 A1 | 9/2006 | Melese et al. | |
| 2006/0225737 A1 | 10/2006 | Lobbi | |
| 2006/0238333 A1 | 10/2006 | Welch et al. | |
| 2006/0278293 A1 | 12/2006 | Weber et al. | |
| 2006/0293921 A1 | 12/2006 | McCarthy et al. | |
| 2007/0013511 A1 | 1/2007 | Weiner et al. | |
| 2007/0049834 A1 | 3/2007 | Tao et al. | |
| 2007/0069887 A1 | 3/2007 | Welch et al. | |
| 2007/0080233 A1 | 4/2007 | Forster et al. | |
| 2007/0135866 A1 | 6/2007 | Baker et al. | |
| 2007/0142731 A1 | 6/2007 | Ye et al. | |
| 2007/0183475 A1 | 8/2007 | Hutcherson | |
| 2007/0185390 A1 | 8/2007 | Perkins et al. | |
| 2007/0189358 A1 | 8/2007 | Lane et al. | |
| 2007/0265533 A1 * | 11/2007 | Tran | A61B 5/02108 600/528 |
| 2008/0033308 A1 | 2/2008 | Cen et al. | |
| 2008/0064967 A1 | 3/2008 | Ide | |
| 2008/0149701 A1 | 6/2008 | Lane | |
| 2008/0175301 A1 | 7/2008 | Chen | |
| 2008/0281167 A1 | 11/2008 | Soderberg et al. | |
| 2008/0281168 A1 | 11/2008 | Gibson et al. | |
| 2008/0300473 A1 | 12/2008 | Benni | |
| 2009/0062674 A1 | 3/2009 | Jin et al. | |
| 2009/0100333 A1 | 4/2009 | Xiao | |
| 2009/0103469 A1 | 4/2009 | Smith et al. | |
| 2009/0105549 A1 | 4/2009 | Smith et al. | |
| 2009/0105566 A1 | 4/2009 | Smith et al. | |
| 2009/0105567 A1 | 4/2009 | Smith et al. | |
| 2009/0131774 A1 | 5/2009 | Sweitzer et al. | |
| 2009/0141124 A1 | 6/2009 | Liu et al. | |
| 2009/0172591 A1 | 7/2009 | Pomper | |
| 2009/0175317 A1 | 7/2009 | Chan et al. | |

(56) References Cited

U.S. PATENT DOCUMENTS

| | | |
|---|---|---|
| 2009/0177248 A1 | 7/2009 | Roberts |
| 2009/0182526 A1 | 7/2009 | Quinn et al. |
| 2009/0196475 A1 | 8/2009 | Demirli et al. |
| 2009/0221880 A1 | 9/2009 | Soderberg et al. |
| 2010/0049077 A1 | 2/2010 | Sadleir et al. |
| 2010/0056928 A1 | 3/2010 | Zuzak |
| 2010/0094098 A1 | 4/2010 | Smith et al. |
| 2010/0094145 A1 | 4/2010 | Ye et al. |
| 2010/0121164 A1 | 5/2010 | Donars et al. |
| 2010/0191472 A1 | 7/2010 | Doniger et al. |
| 2010/0265986 A1 | 10/2010 | Mullin et al. |
| 2010/0280331 A1 | 11/2010 | Kaufman et al. |
| 2010/0284436 A1 | 11/2010 | Lane et al. |
| 2010/0298650 A1 | 11/2010 | Moon et al. |
| 2010/0322282 A1 | 12/2010 | Lane et al. |
| 2010/0324380 A1 | 12/2010 | Perkins et al. |
| 2011/0047298 A1 | 2/2011 | Eaton et al. |
| 2011/0054267 A1 | 3/2011 | Fidacaro et al. |
| 2011/0112791 A1 | 5/2011 | Pak et al. |
| 2011/0121978 A1 | 5/2011 | Schwörer et al. |
| 2011/0140896 A1 | 6/2011 | Menzel |
| 2011/0148622 A1 | 6/2011 | Judy et al. |
| 2011/0152629 A1 | 6/2011 | Eaton et al. |
| 2011/0158283 A1 | 6/2011 | Meyerson et al. |
| 2011/0178376 A1 | 7/2011 | Judy et al. |
| 2011/0199203 A1 | 8/2011 | Hsu |
| 2011/0228810 A1 | 9/2011 | O'Hara et al. |
| 2011/0228811 A1 | 9/2011 | Fraden |
| 2011/0230731 A1 | 9/2011 | Rantala et al. |
| 2011/0237906 A1 | 9/2011 | Kabakov |
| 2011/0251493 A1 | 10/2011 | Poh et al. |
| 2011/0276698 A1 | 11/2011 | Bigioi et al. |
| 2011/0282168 A1* | 11/2011 | Weiss ................. A61B 5/7465 600/323 |
| 2011/0285248 A1 | 11/2011 | Cewers |
| 2011/0286644 A1 | 11/2011 | Kislal |
| 2011/0291837 A1 | 12/2011 | Rantala |
| 2011/0291838 A1 | 12/2011 | Rantala |
| 2012/0004516 A1 | 1/2012 | Eng et al. |
| 2012/0005248 A1 | 1/2012 | Garudadr et al. |
| 2012/0022348 A1 | 1/2012 | Droitcour et al. |
| 2012/0026119 A1 | 2/2012 | Judy et al. |
| 2012/0053422 A1 | 3/2012 | Rantala |
| 2012/0094600 A1 | 4/2012 | DelloStritto et al. |
| 2012/0096367 A1 | 4/2012 | DelloStritto et al. |
| 2012/0130197 A1 | 5/2012 | Kugler et al. |
| 2012/0130251 A1 | 5/2012 | Huff |
| 2012/0130252 A1 | 5/2012 | Pohjanen et al. |
| 2012/0136559 A1 | 5/2012 | Rothschild |
| 2012/0150482 A1 | 6/2012 | Yildizyan et al. |
| 2012/0154152 A1 | 6/2012 | Rantala et al. |
| 2012/0165617 A1 | 6/2012 | Vesto et al. |
| 2012/0179011 A1 | 7/2012 | Moon et al. |
| 2012/0242844 A1 | 9/2012 | Walker et al. |
| 2012/0271130 A1 | 10/2012 | Benni |
| 2012/0302905 A1 | 11/2012 | Kaski |
| 2012/0319848 A1 | 12/2012 | Coffeng |
| 2013/0002420 A1 | 1/2013 | Perkins et al. |
| 2013/0006093 A1 | 1/2013 | Raleigh et al. |
| 2013/0023772 A1 | 1/2013 | Kinsley et al. |
| 2013/0035599 A1 | 2/2013 | De Bruijn et al. |
| 2013/0053655 A1* | 2/2013 | Castellanos ............. A61B 8/06 600/440 |
| 2013/0085348 A1 | 4/2013 | Devenyi et al. |
| 2013/0085708 A1 | 4/2013 | Sattler |
| 2013/0085758 A1 | 4/2013 | Csoma et al. |
| 2013/0086122 A1 | 4/2013 | Devenyi et al. |
| 2013/0109927 A1 | 5/2013 | Menzel |
| 2013/0109929 A1 | 5/2013 | Menzel |
| 2013/0137939 A1 | 5/2013 | He et al. |
| 2013/0138003 A1 | 5/2013 | Kaski |
| 2013/0172770 A1 | 7/2013 | Muehlsteff |
| 2013/0178719 A1 | 7/2013 | Balji et al. |
| 2013/0211265 A1 | 8/2013 | Bedingham et al. |
| 2013/0215928 A1 | 8/2013 | Bellifemine |
| 2013/0245457 A1 | 9/2013 | Kinsley et al. |
| 2013/0245462 A1 | 9/2013 | Capdevila et al. |
| 2013/0245467 A1 | 9/2013 | St. Pierre et al. |
| 2013/0245488 A1 | 9/2013 | Quinn et al. |
| 2013/0245489 A1 | 9/2013 | Mullin et al. |
| 2013/0265327 A1 | 10/2013 | Vann et al. |
| 2013/0267792 A1 | 10/2013 | Petersen et al. |
| 2013/0267793 A1 | 10/2013 | Meador et al. |
| 2013/0267861 A1 | 10/2013 | Vassallo et al. |
| 2013/0267873 A1 | 10/2013 | Fuchs |
| 2013/0268283 A1 | 10/2013 | Vann et al. |
| 2013/0271283 A1 | 10/2013 | Judy et al. |
| 2013/0271591 A1 | 10/2013 | Van Leest et al. |
| 2013/0296716 A1 | 11/2013 | Kurzenberger |
| 2013/0307536 A1 | 11/2013 | Feng et al. |
| 2013/0322729 A1 | 12/2013 | Mestha et al. |
| 2013/0334298 A1 | 12/2013 | Sakpal et al. |
| 2013/0342691 A1 | 12/2013 | Lewis et al. |
| 2014/0003461 A1 | 1/2014 | Roth |
| 2014/0003462 A1 | 1/2014 | Roth |
| 2014/0031637 A1 | 1/2014 | Fidacaro et al. |
| 2014/0032241 A1 | 1/2014 | Coffeng |
| 2014/0058213 A1 | 2/2014 | Abu-Tarif et al. |
| 2014/0171805 A1 | 2/2014 | Mullin et al. |
| 2014/0064327 A1 | 3/2014 | Roth |
| 2014/0064328 A1 | 3/2014 | Roth |
| 2014/0064333 A1 | 3/2014 | Roth |
| 2014/0072190 A1 | 3/2014 | Wu et al. |
| 2014/0072228 A1 | 3/2014 | Rubinstein |
| 2014/0072229 A1 | 3/2014 | Wadhwa |
| 2014/0073860 A1 | 3/2014 | Uriti |
| 2014/0088434 A1 | 3/2014 | Roth |
| 2014/0088435 A1 | 3/2014 | Roth |
| 2014/0088436 A1 | 3/2014 | Roth |
| 2014/0088446 A1 | 3/2014 | St. Pierre et al. |
| 2014/0112367 A1 | 4/2014 | Roth |
| 2014/0114600 A1 | 4/2014 | Roth |
| 2014/0121481 A1 | 5/2014 | Abrams et al. |
| 2014/0155759 A1 | 6/2014 | Kaestle et al. |
| 2014/0189576 A1 | 7/2014 | Carmi |
| 2014/0221766 A1 | 8/2014 | Kinast |
| 2014/0221796 A1 | 8/2014 | Lia et al. |
| 2014/0232516 A1 | 8/2014 | Stivoric et al. |
| 2014/0235963 A1 | 8/2014 | Edwards et al. |
| 2014/0247058 A1 | 9/2014 | Mortara |
| 2014/0253709 A1 | 9/2014 | Bresch et al. |
| 2014/0321505 A1 | 10/2014 | Rill et al. |
| 2014/0330098 A1 | 11/2014 | Merritt et al. |
| 2014/0331298 A1 | 11/2014 | Baker et al. |
| 2015/0025344 A1 | 1/2015 | Benni |
| 2015/0036350 A1 | 2/2015 | Palikaras et al. |
| 2015/0045663 A1 | 2/2015 | Palikaras et al. |
| 2015/0073828 A1 | 3/2015 | Mortara et al. |
| 2015/0077268 A1 | 3/2015 | Lane et al. |
| 2015/0088538 A1 | 3/2015 | Dykes et al. |
| 2015/0110153 A1 | 4/2015 | Hoblit et al. |
| 2015/0126847 A1 | 5/2015 | Balji et al. |
| 2015/0157275 A1 | 6/2015 | Swamy et al. |
| 2015/0182114 A1 | 7/2015 | Wang et al. |
| 2015/0201872 A1 | 7/2015 | Benni |
| 2015/0257653 A1 | 9/2015 | Hyde et al. |
| 2015/0265159 A1 | 9/2015 | Lane et al. |
| 2015/0272452 A1 | 10/2015 | Mullin et al. |
| 2015/0308946 A1 | 10/2015 | Duffy et al. |
| 2015/0327811 A1 | 11/2015 | Mortara |
| 2015/0339805 A1 | 11/2015 | Ohba |
| 2016/0000335 A1 | 1/2016 | Khachaturian et al. |
| 2016/0007922 A1 | 1/2016 | Sen et al. |
| 2016/0035084 A1 | 2/2016 | Khachaturian et al. |
| 2016/0051171 A1 | 2/2016 | Pikov et al. |
| 2016/0136367 A1 | 5/2016 | Varney |
| 2016/0150978 A1 | 6/2016 | Yuen et al. |
| 2016/0157739 A1* | 6/2016 | Peeters ................. A61B 5/4836 600/479 |
| 2016/0302666 A1 | 10/2016 | Shaya et al. |
| 2016/0361002 A1 | 12/2016 | Palikaras et al. |
| 2017/0238816 A1* | 8/2017 | Nakazawa ......... A61B 5/02108 |
| 2019/0167195 A1 | 6/2019 | Axelrod et al. |

(56) References Cited

U.S. PATENT DOCUMENTS

| | | | |
|---|---|---|---|
| 2019/0336016 A1 | 11/2019 | Zhao et al. | |
| 2019/0336077 A1* | 11/2019 | Kuhn | A61B 5/486 |
| 2019/0350470 A1 | 11/2019 | Khachaturian et al. | |

FOREIGN PATENT DOCUMENTS

| | | |
|---|---|---|
| CN | 102198004 A | 9/2011 |
| CN | 202619644 U | 4/2013 |
| CN | 202859096 U | 4/2013 |
| CN | 203861234 U | 10/2014 |
| CN | 105662434 A | 4/2016 |
| CN | 105919601 A | 9/2016 |
| CN | 206342477 U | 7/2017 |
| CN | 206443702 U | 8/2017 |
| DE | 19827343 A1 | 12/1999 |
| EP | 0404562 A2 | 11/1991 |
| EP | 0537383 A1 | 4/1993 |
| EP | 0630203 B1 | 12/1994 |
| EP | 2045590 A1 | 4/2009 |
| EP | 2380493 A1 | 10/2011 |
| EP | 2674735 A1 | 12/2013 |
| EP | 2836107 A1 | 2/2015 |
| GB | 2291498 A | 1/1996 |
| GB | 2500719 A1 | 10/2013 |
| GB | 1322906.7 A | 1/2015 |
| GB | 2521620 A | 1/2015 |
| GB | 2523741 A | 9/2015 |
| JP | 2002527136 A | 8/2002 |
| WO | 1992002792 A1 | 2/1992 |
| WO | 1998001730 A1 | 1/1998 |
| WO | 1999039166 A1 | 8/1999 |
| WO | 1999067611 A1 | 12/1999 |
| WO | 2000021437 A3 | 7/2001 |
| WO | 2005024710 A1 | 3/2005 |
| WO | 2005024712 A1 | 3/2005 |
| WO | 2005078636 A3 | 1/2006 |
| WO | 2008053474 A2 | 5/2008 |
| WO | 2011013132 A1 | 2/2011 |
| WO | 2011063266 A2 | 5/2011 |
| WO | 2012093311 A1 | 7/2012 |
| WO | 2013144559 A1 | 10/2013 |
| WO | 2013144652 A1 | 10/2013 |
| WO | 2014082071 A1 | 5/2014 |
| WO | 2015049268 A1 | 4/2015 |
| WO | 2015128657 A1 | 9/2015 |
| WO | 2015154105 A1 | 10/2015 |
| WO | 2016005050 A1 | 1/2016 |
| WO | 2016040540 A1 | 3/2016 |
| WO | 2016054079 A1 | 4/2016 |
| WO | 2016120870 A1 | 8/2016 |
| WO | 2017120615 A3 | 7/2017 |
| WO | 2017125397 A1 | 7/2017 |

OTHER PUBLICATIONS

Kim, Harry, International Search Report and Written Opinion issued by the US International Searching Authority regarding PCT/US21/34164, dated Sep. 8, 2021, 12 pages.

Pitzer et al., Detection of Hypoglycemia With the 3 GlucoWatch Biographer, Diabetes Care, vol. 24, No. 5, May 2001, pp. 881-885, retrieved from the nternet from http://citeseerx.isl.psu.edu/viewdoc/download?doi=10.1.1.915.1360&rep=rep1 &type=pdf on Nov. 9, 2018.

Balakrishnan, Guha, Fredo Durand, and John Guttag. "Detecting pulse from head motions in video." Computer Vision and Pattern Recognition (CVPR), 2013 IEEE Conference on. IEEE, 2013.

Islam, S. M. R., et al., "Internet of Things for Health Care: A Comprehensive Survey", Jun. 1, 2015, Digital Object dentifier 10.1109/ACCESS.2015.2437951, IEEE Access vol. 3, 2015, retrieved from the Internet on Oct. 1, 2018.

Hassanalieragh Moon, et al., Health Monitoring and Management Using Internet-0f-Things (IoT) Sensing with Cloud-based Processing: Opportunities and Challenges, 2015 IEEE International Conference on Services Computing, pp. 285-292, 978-1-4673-7281-7/15, DOI 10.1109/SCC.2015.47, retrieved from the Internet on Oct. 1, 2018.

Covidien, Filac 3000 EZ-EZA Electronic Thermometer Operating Manual, 2012, http://www.covidien.com/mageServer.aspx?contentID=31819&contenttype=application/pdf, retrieved from the Internet on Jul. 24, 2015.

Gravina et al., Multi-Sensor Fusion in Body Sensor Networks: State-of-the-art and research challenges, DOI: 10.1016/j.inffus.2016.09.005, Information Fusion, Sep. 13, 2016, retrieved from the Internet on Oct. 1, 2018 at https://www.researchgate.net/publication/308129451.

Klonoff, David C., Noninvasive Blood Glucose Monitoring, Diabetes Care, vol. 20, No. 3, Mar. 1997, pp. 133-437, DOI: 10.2337/diacare.20.3.433, Source: PubMed, retrieved from the Internet on Oct. 2, 2018.

Rossetti et el., Estimating Plasma Glucose from Interstitial Glucose: The Issue of Calibration Algorithms in Commercial Continuous Glucose Monitoring Devices, Sensors 2010, 10, 10936-10952; doi:10.3390/s101210936, SSN 1424-8220, retrieved from www.mdpi.com/journal/sensors on Oct. 2, 2018.

Gautama, T. and Van Hulle, M., "A phase-based approach to the estimation of the optical flow field using spatial lltering", Neural Nellvorks, IEEE Transactions, 13(5): 1127-1136 (Sep. 2002).

Vole, "Non-Invasive Glucose Monitoring Patent Landscape", KnowMade, 2405 route des Dolines, 06902 Sophia Antipolis, France, Tel: +33 489 89 16 20, http://www.knowmade.com, retrieved from the Internet on Oct. 2, 2018, published Sep. 2015.

Berger, Andrew J., Multicomponent blood analysis by near-infrared Raman spectroscopy, Applied Optics, vol. 38, No. 13, May 1, 1999, pp. 2916-2926, retrieved from the Internet on Oct. 2, 2018.

Darwish et al., Wearable and Implantable Wireless Sensor Network Solutions for Healthcare Monitoring, Sensors 2011, 11, 5561-5595; doi: 10.3390/s110605561, ISSN 1424-8220, retrieved from www.mdpi.com/joumal/sensors on Oct. 2, 2018.

Oiver et al., Glucose sensors: a review of current and emerging technology, Diabetic Medicine, 26, pp. 197-210, 2009 Diabetes UK, retrieved from https://onlinelibrary.wiley.com/doi/epdf/10.1111/j.1464-5491.2008.02642.x on Oct. 2, 2018.

Jurik, Andrew D. et al., Remote Medical Monitoring, University of Virginia, retrieved from http://www.cs.virginia.edu/urik/docs/jurik-rmm-2008 pdf on Oct. 1, 2018.

Tura, Andrew et al., A Low Frequency Electromagnetic Sensor for Indirect Measurement of Glucose Concentration: In Vitro Experiments in Different Conductive Solutions, Sensors 2010, 10, 5346-5358; doi: 10.3390/s100605346, ISSN 1424-8220, retrieved from www.mdpi.com/journal/sensors on Oct. 2, 2018.

Rubinstein, M., et al., "Motion denoising with application to limelapse photography," IEEE Computer Vision and Pattern Recognition, CVPR, pp. 313-320 (Jun. 2011).

Pfotzner, Andreas et al., Evaluation of System Accuracy of the GlucoMen LX Plus Blood Glucose Monitoring System With Reference to ISO 15197:2013, Journal of Diabetes Science and Technology 2016, vol. 10(2) 618-619, Diabetes Technology Society, DOI: 10.1177/1932296815613803, retrieved from https://www.ncbi.nlm.nih.gov/pmc/~rticles/PMC4 773971 /pdf/10 .1177 1932296815613803 .pdf on Nov. 2, 2018.

Poveda, Carlos G. Juan, Fundamentals of Microwave , Techcnology for Non-Invasive Blood Glucose Monitoring And Review of the Most Significant Works Developed, Revista Doctorado UMH vol. 1, n°1, 2015—Articulo p6, PhD Program on Industrial and Telecommunication Technologies {TECNIT) nBio Research Group at Systems Engineering Department, Miguel Hernandez University, Elche, Spain, Apr. 2015, retrieved from https://www.researchgate.net/publication/298715332 on Nov. 2, 2018.

Timoner Samson J., and Dennis M. Freeman. "Multi-image gradient-based algorithms for motion estimation." Optical engineering 40.9 (2001): 2003-2016.

Saha et al., A Glucose Sensing System Based on Transmission Measurements at Millimetre Waves using Micro strip Patch Antennas, Scientific Reports, 7: 6855, DOI: 10.1038/s41598-017-06926-

(56) References Cited

OTHER PUBLICATIONS

1, Jul. 31, 2017, retrieved from https://www.ncbi.nlm.nih.gov/pmc/articles/PMC5537249/pdf/41598_2017 Article_6926.pdf on Nov. 2, 2018.

Verkruysse, Wim, Lars 0. Svaasand, and J_ Stuart Nelson. "Remote plethysmographic imaging using ambient ighl." Optics express 16.26 (2008): 21434-21445.

Todd, Catherine, et al., Towards Non-Invasive Extraction and Determination of Blood Glucose Levels, Bioengineering 2017, 4, 82, Sep. 27, 2017, retrieved from https://www.ncbi.nlm.nih.gov/pmc/articles/PMC5746749/pdf/bioengineering-04-00082.pdf on Nov. 2, 2018.

Pfotzner, Andreas, Journal of Diabetes Science and Technology 2016, vol. 10(1) 101-103, Diabetes Technology Society, DOI: 10.1177/1932296815619183, retrieved from retrieved from www.mdpi.com/joumal/sensors on Nov. 2, 2018.

Stankovic, John A., Wireless Sensor Networks, Department of Computer Science, University of Virginia Charlottesville, Virginia 22904, Jun. 19, 2006, retrieved from https://www.cs.virginia.edu/-slankovic/psfiles/wsn.pdf on Oct. 1, 2018.

Wang J., et al., "The cartoon animation filter," ACM Trans. Graph., 25:1169-1173 (2006).

Lai, Xiaochen et al., A Survey of Body Sensor Networks, Sensors 2013, 13, 5406-5447; doi: 10.3390/s130505406, ISSN 1424-8220, retrieved from www.mdpi.com/journal/sensors on Oct. 1, 2018.

Bruen et al., Glucose Sensing for Diabetes Monitoring: Recent Developments, Sensors DOI:10.3390/s17081866, Aug. 12, 2017, retrieved from https://pdfs.semanticscholar.org/9a8b/8f1abdd11eae279204c81dbb5525fe473106.pdf?_ga=2.60896047.2075682402.1541162314-1823527149.1541162314 on Nov. 2, 2018.

Facchinetti, Andrea, Continuous Glucose Monitoring Sensors: Past, Present and Future Algorithmic Challenges, Sensors 2016, 16(12), 2093; https://doi.org/10.3390/s16122093, Dec. 9, 2016, retrieved from https://pdfs.semanticscholar.org/6dc 7 /75fb 79fc 7 ca85d795d8f520d79a03ea45311 .pdf?_ga=2.91420569.2075682402. 1541162314-1823527149.1541162314 on Nov. 2, 2018.

Larin, Kirill V., et al., Noninvasive Blood Glucose Monitoring With Optical Coherence Tomography, Diabetes Care, vol. 25, No. 12, Dec. 2002, retrieved from the Internet on Oct. 2, 2018.

Chung et al., Simultaneous Measurements of Glucose, Glutamine, Ammonia, Lactate, and Glutamate in Aqueous Solutions by Near-Infrared Spectroscopy, DOI: 10.1366/0003702963906447, Applied Spectroscopy, Feb. 1996, retrieved from www.researchgate.com on Oct. 2, 2018.

R. Fisher, S. Perkins, A. Waiker and E. Wolfart, Frequency Filter, Image Processing Learning Resources, J003, retrieved from the Internet on Jun. 24, 2014 at http://homepages.inf.ed.ac.uk/rbf/HIPR2/freqfilt.htm.

Bandodkar et al., Tattoo-Based Noninvasive Glucose Monitoring: A Proof-0f-Concept Study, dx.doi.org/10.1021/ac504300n, Anal. Chem. 2015, 87, 394-398, American Chemical Society, retrieved from the internet on Oct. 2, 2018 at https://pubs.acs.org/doi/pdf/10.1021/ac504300n.

Grose, Julianne H. et al., The Role of PAS Kinase in PASsing the Glucose Signal, Sensors 2010, 10, 5668-5682; doi:10.3390/s100605668, ISSN 1424-8220, www.mdpi.com/journal/sensors, Jun. 4, 2010, retrieved from the Internet on Oct. 2, 2018.

Fernandez, Clara Rodriguez, Needle-Free Diabetes Monitoring: An Interview with the Founder of GlucoWise, Nov. 28, 2016, Labiotech IG, retrieved from the Internet on Oct. 1, 2018.

Routh, Fourier Transform, Glucose Sensing Neurons in the Ventromedial Hypothalamus, Sensors 2010, 10, 9002-9025; doi: 10.3390/s101009002, ISSN 1424-8220, www.mdpi.com/joumal/sensors, Aug. 10, 2010, retrieved from he Internet on Oct. 2, 2018 at https://www.researchgate.net/publication/4 7369031 _Glucose_ Sensing Neurons in_ the_ Ventromedial_ Hypothalamus/download, p. 9009.

Choi, Heungjae et al., Design and In Vitro Interference Test of Microwave Noninvasive Blood Glucose Monitoring Sensor, IEEE Trans Microw Theory Tech. Oct. 1, 2015; 63(10 PI 1): 3016-3025, doi: 10.1109/TMTT.2015.2472019, PMCID: PMC4641327, EMSID: EMS65843, PMID: 26568639, retrieved from the Internet on Oct. 2, 2018.

Yilmaz, Tuba et al., Detecting Vital Signs with Wearable Wireless Sensors, Sensors 2010, 10, 10837-10862 doi:10.3390/s101210837, ISSN 1424-8220, Dec. 2, 2010, retrieved from www.mdpi.com/journal/sensors on Oct. 2, 2018.

Vashist, Sandeep Kumar, Non-Invasive Glucose Monitoring Technology in Diabetes Management: A Review, Analytica Chimica Acta 750 (2012) 16-27, NUS Nanosience and Nanotechnology Initiative (NUSNNI) NanoCore, National University of Singapore, T-Lab Level 11, 5A Engineering Drive 1, Singapore 117580, Singapore, Elsevier B.V., Apr. 2, 2012, retrieved from the Internet on Oct. 2, 2016.

Hao-Yu Wu, Eulerian Video Magnification for Revealing Subtle Changes in the World, ACM Transactions on Graphics (TOG)—SIGGRAPH 2012 Conference Proceedings, vol. 31 Issue 4, Jul. 2012, Article No. 65, ACM New 39 York, NY, USA, ISSN: 0730-0301 EISSN: 1557-7368 doi 10.1145/2185520.2185561, published on Jul. 1, 2012, etrieved from the Internet on Jul. 9, 2014 from http://people.csail.mil.edu/billf/publications/Eulearian_Video_Magnification.pdf.

Eduardo S.L. Gastal, Adaptive Manifolds for Real-Time High-Dimensional Filtering, ACM Transactions on Graphics (TOG)—SIGGRAPH 2012 Conference Proceedings, vol. 31 Issue 4, Jul. 2012, Article No. 33, ACM New York, NY, USA, ISSN: 0730-0301 EISSN: 1557-7368, doi10.1145/2185520.2185529, retrieved from the Internet on on Jul. 9, 2013 from http://inf.ufrgs.br/-eslgastal/AdaptiveManifolds/Gastal Oliveira SIGGRAPH2012 Adaotive Manifolds.pdf.

Sunghyun Cho, Video deblurring for hand-held cameras using patch-based synthesis, ACM Transactions on Graphics (TOG)—SIGGRAPH 2012 Conference Proceedings, vol. 31 Issue 4, Jul. 2012, Article No. 64, ACM New Fork, NY, USA, ISSN: 0730-0301 EISSN: 1557-7368 doi 10.1145/2185520.2185561, published on Jul. 1, 2012, retrieved from the Internet on Jul. 9, 2014 from http://juew.org/publication/video_deblur.pdf.

C. Liu, Motion magnification, ACM SIGGRAPH 2005, pp. 519-526, 2005, retrieved from http://people.csail.mil.edu/celiu/pdfs/motionmagpdf on Jul. 9, 2014.

O. Ari Kan, Interactive Motion Generation from Examples, ACM Transactions on Graphics (TOG), Proceedings of ACM SIGGRAPH 2002, vol. 21 Issue 3, Jul. 2002, pp. 483-490, ACM New York, NY, USA, SBN:1-58113-521-1, doi 10.1145/566654.566606, retrieved from the Internet on Jul. 9, 2014 from http://www.okanarikan.com/Papers/SynthesisFromExamples/paper.pdf.

John L. Smith, The Pursuit of Noninvasive Glucose: "Hunting the Deceitful Turkey", Fourth Edition, 2015, retrieved from the Internet on Oct. 1, 2018 from http://www.mendosa.com/The%20Pursuit%20of"/o20Noninvsive%20Glucose,%20Fourth%20Edition.pdf.

Yali Zheng, Unobtrusive Sensing and Wearable Devices for Health Informatics, IEEE Transactions on Biomedical Engineering, Mar. 2014, Doi: 10.1109/TBME.2014.2309951, retrieved from the Internet on Oct. 1, 2018 from https://www.researchgate.net/publication/260419901.

Yitzhak Mendelson, Pulse Oximetry: Theory and Applications for Noninvasive Monitoring, CUN.CHEM. 38/9, 1601-1607, (1992), retrieved from the Internet on Oct. 2, 2018.

Stephen F. Mallin, Noninvasive Prediction of Glucose by Near-Infrared Diffuse Reflectance Spectroscopy, Clinical Chemistry 45:9, 1651-1658 (1999), Oak Ridge Conference, retrieved from the Internet on Oct. 2, 2018 from http://clinchem.aaccjnls.org/contenl/clinchem/45/9/1651.full.pdf.

Thennadil et al., Comparison of Glucose Concentration in Interstitial Fluid, and Capillary and Venous Blood During Rapid Changes in Blood Glucose Levels, Diabetes Technology & Therapeutics, vol. 3, No. 3, 2001, Mary Ann iebert, Inc., retrieved from the Internet on Oct. 2, 2018 from http://thenemiirblog.ubiquilighl.com/pdf/GlucoseInterstitialvCapillarywVenous.pdf.

Khalil et al., Non-lnvasive Glucose Measurement Technologies: An Update from 1999 to the Dawn of the New Millennium, Diabetes Technology & Therapeutics, vol. 6, No. 5, 2004, Mary Ann Liebert,

(56) References Cited

OTHER PUBLICATIONS

Inc., retrieved from the Internet on Oct. 2, 2018 from http://bme240.eng.uci.edu/students/06s/eclin/articles/long.pdf.
Caduff et al., First human experiments with a novel non-invasive, non-optical continuous glucose monitoring system. Biosensors and Bioelectronics xxx (2003) 1-9, retrieved from the Internet on Oct. 2, 2018.

\* cited by examiner

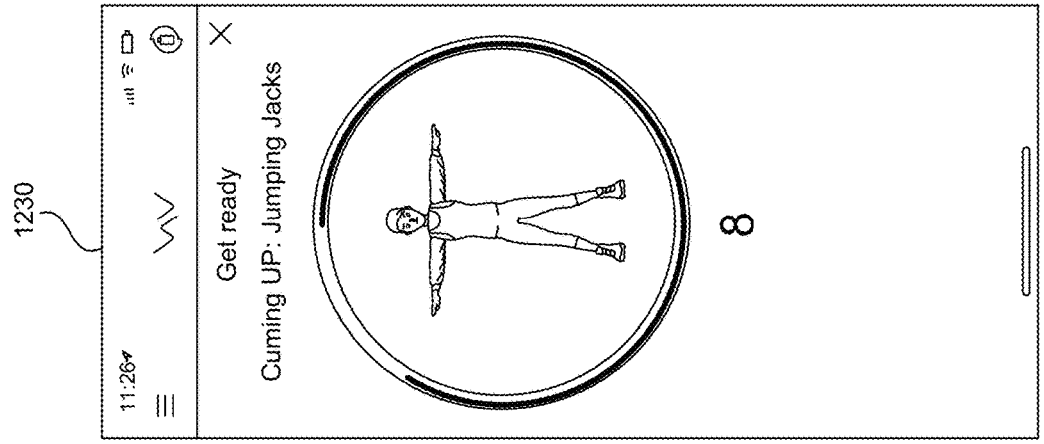
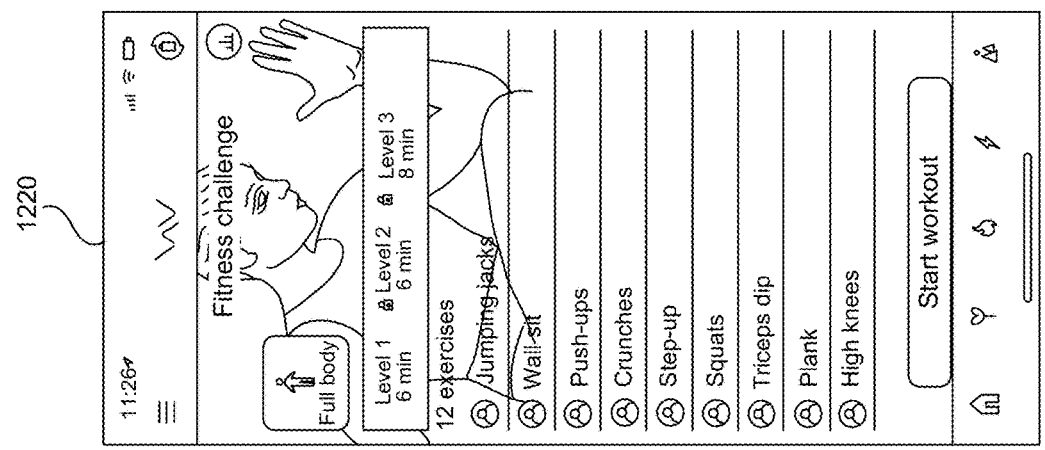
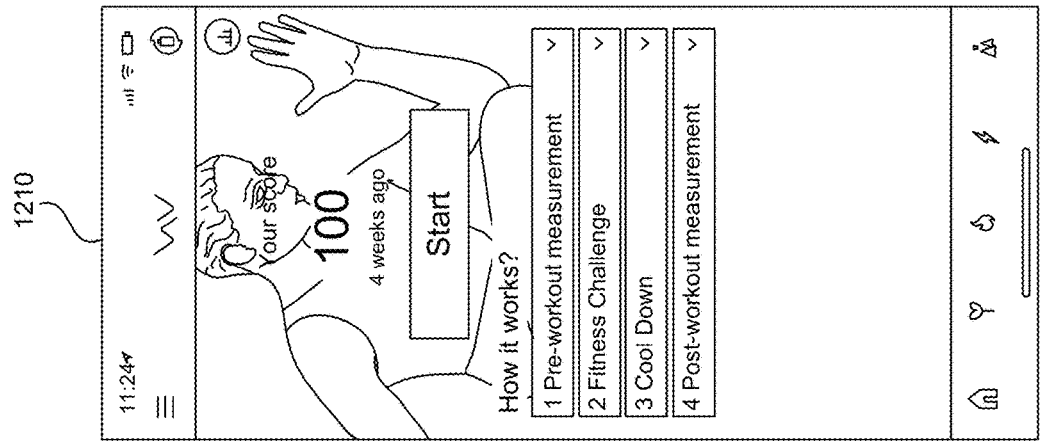
FIG. 29

APPARATUS AND METHODS FOR MEASURING BLOOD PRESSURE AND OTHER VITAL SIGNS VIA A FINGER

CROSS REFERENCE TO RELATED APPLICATIONS

This application claims the benefit of U.S. Provisional Patent Application Ser. No. 63/033,006, filed Jun. 1, 2020, entitled "Apparatus and Method for Measuring Vital Signs" ("the Provisional Application"). The Provisional application is incorporated herein by reference in its entirety as if the contents thereof had been stated herein.

Subject to the following clarifications and qualifications, the following U.S. patents and U.S. Patent Publications (collectively "the References") are also incorporated herein by reference in their entireties as if the contents thereof had been stated herein. No subject matter of the References that is contrary to the instant disclosure is incorporated herein. No claims of the References are incorporated herein. In the event of inconsistencies between this disclosure and the References, the References should be considered supplementary hereto, and the instant disclosure controls in the event of any irreconcilable inconsistencies. Information in the References is incorporated herein only to the extent that no conflict exists between such information this disclosure. In the event of a conflict that would render any claim hereof invalid, then such conflicting information is specifically not incorporated by reference herein. The foregoing disclaimers do not apply to the Provisional application. The References are U.S. Pat. Nos. 8,950,935; 10,492,684; and 10,485,431; and U.S. Published Patent Application No. 2018-0235478A1.

TECHNICAL FIELD

This disclosure relates generally to systems and methods for measuring blood pressure alone or in combination with one or more other non-blood pressure vital signs such as hematocrit, total protein, blood glucose levels, $SpO_2$, pulse rate, respiratory rate, temperature, EEG, and others, in a mammal, such as a human, via a finger.

BACKGROUND

As used herein, the terms monitor/monitoring, measure/measuring, capture/capturing, detect/detecting, and sense/sensing are used synonymously, unless the context in which they are used suggests otherwise. Likewise, the terms user and subject, pulse rate and heart rate, pulse oximetry and SpO2, pump and pneumatic engine, and physiological characteristics and vital signs are used synonymously, unless the context in which they are used suggests otherwise. Accordingly, and subject to the foregoing exception, such terms may be considered to have been used interchangeably throughout.

Prior techniques of measuring blood pressure typically employ an arm cuff, or optical measurements taken at the fingertip. The use of an arm cuff can be inconvenient, awkward and/or painful. The use of optical measurements, such as miniature dynamic light scattering (mDLS) to derive an indication of blood pressure, pulse rate, and other related vital signs, via the finger requires complex circuitry and algorithms, and the results may not provide an accurate or consistent indication of blood pressure. In addition, it may be desirable to obtain measurements of non-blood pressure vital signs at the same time that blood pressure is being measured. Applying sensors to a subject, in addition to an arm cuff, to obtain these measurements, can be awkward, inconvenient and/or impractical.

BRIEF DESCRIPTION

There is disclosed an apparatus, system and method for measuring blood pressure via one's finger using an inflatable cuff adapted to receive the finger. The cuff is disposed within and secured to a rigid housing. The cuff is adapted to receive, and when inflated, fully envelope and contact substantially the entirety of the periphery of the portion of the finger in the cuff. The apparatus comprises a pump for inflating the cuff to apply pressure to the subject's finger, a relief valve for deflating the cuff, a pressure sensor for measuring the air pressure in the bladder (and applied to the finger), circuitry for controlling the pump and relief valve and for receiving data from the pressure sensor and other sensors for calculating an indication of the subject's blood pressure using the oscillometric method. Pulse rate may also be calculated using this apparatus. The disclosed apparatus and methods negate any need for the use of light, light sensors, optical measurements, or the use of any other type of electromagnetic radiation (or measurement thereof) to provide an indication of blood pressure.

In addition, there are disclosed embodiments for measuring one or more of the following vital signs, in addition to, or other than, blood pressure and pulse rate, in a manner that is simple and easy for a user: blood glucose levels, heart rate variability, respiration rate, SpO2, blood flow, total hemoglobin (SpHb), PVi, methemoglobin (SpMet), acoustic respiration rate (RRa), carboxyhemoglobin (SpCO), oxygen reserve index (ORi), oxygen content (SpOC), hematocrit (Hc), total protein (TP), EEG and temperature.

A display provides visual indications of vital signs. The apparatus may also communicate with a smartphone equipped with an app for generating and displaying health scores and for communicating vital sign data to a remote patient monitoring system.

BRIEF DESCRIPTION OF THE DRAWINGS

The description of the drawings below refers to various embodiments of apparatuses, systems and methods for implementing a vital sign measuring device (VSMD) and are not intended to limit the scope of the disclosure, and/or the inventions described therein, except as set forth in the appended claims.

FIG. 29 illustrates exemplary displays on a smartphone running an app for a fitness test that measures vital signs before and after exercise and calculates a fitness score.

DETAILED DESCRIPTION

Figure 1:
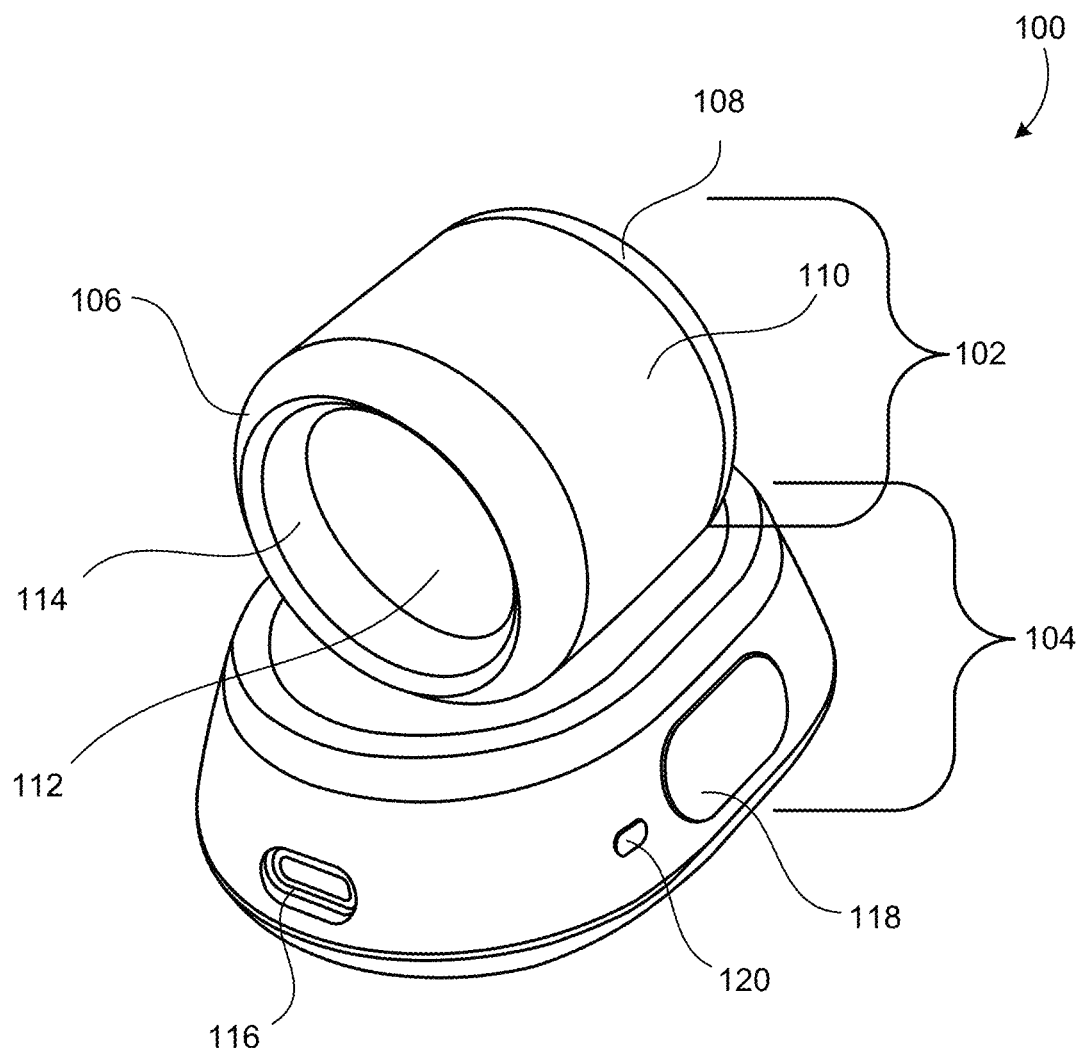
FIG. 1 is a perspective view of a VSMD that employs an inflatable cuff for measuring blood pressure and pulse rate, and that also employs a temperature sensor for measuring temperature.
Figure 2:
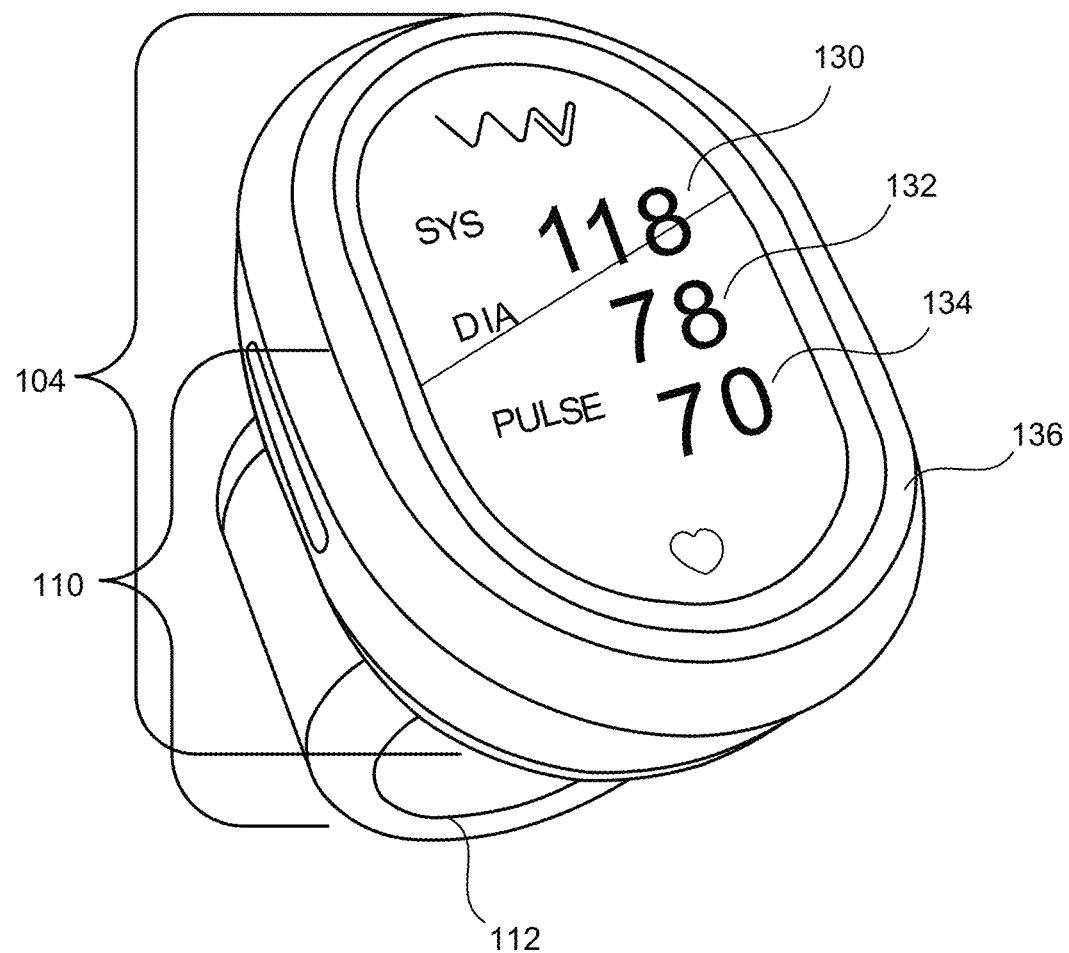
FIG. 2 is a bottom view of the VSMD of FIG. 1 and illustrates a display thereof.
Figure 3:
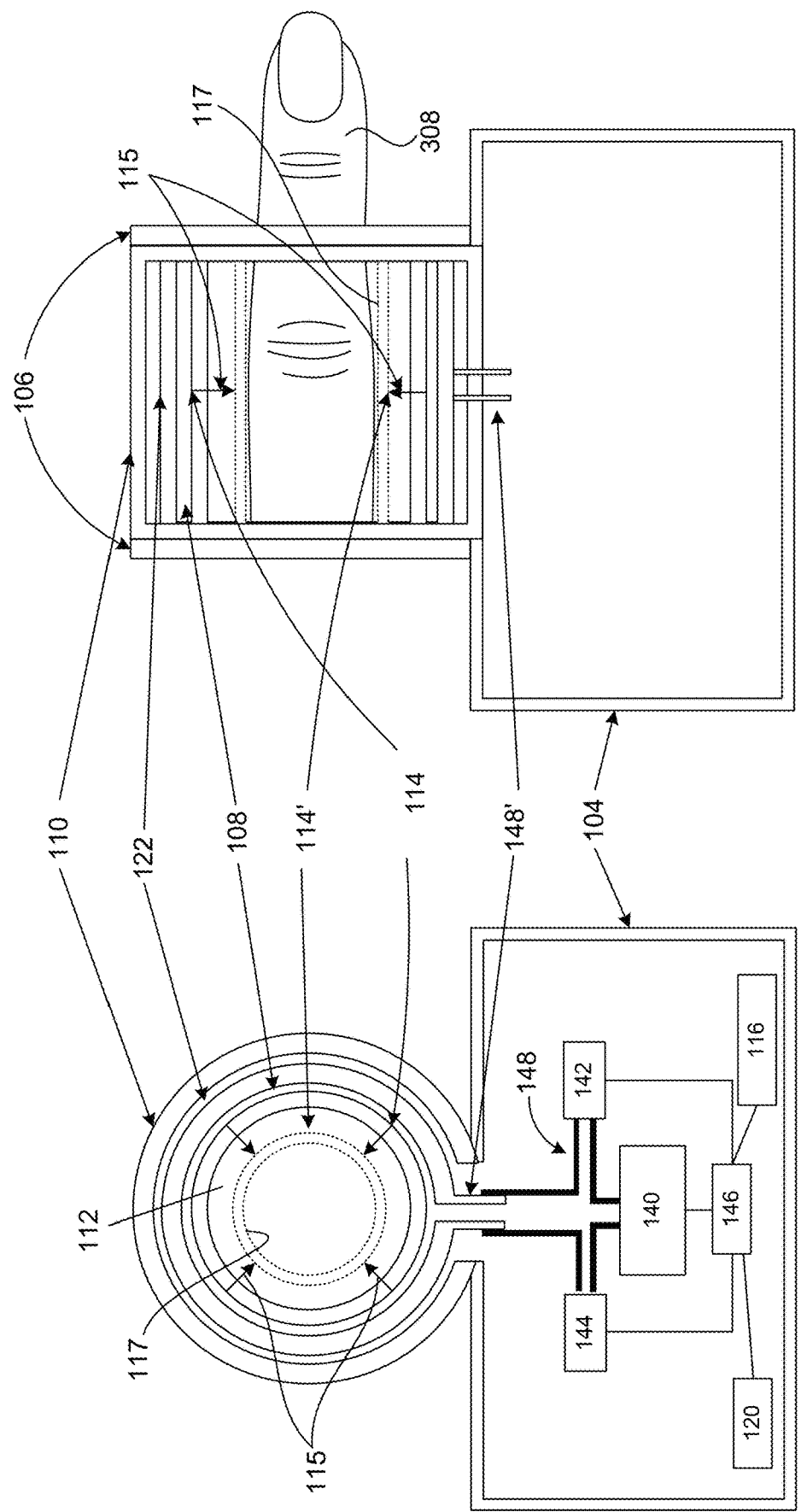
FIG. 3A is a cutaway view of the cuff of the VSMD of FIG. 1 showing various details thereof, and a block diagram of the base showing components that may be contained therein.
FIG. 3B is a side cutaway view of the VSMD shown in FIG. 1, rotated 90° relative to the view of FIG. 3A.

Referring to the drawings, wherein like numerals represent like elements, there is shown in FIGS. 1, 2 and 3, one embodiment of a VSMD 100 for measuring blood pressure and pulse rate. The VSMD 100 comprises a cuff 102 affixed to a base 104. The cuff 102 comprises a hard outer shell 110 that securely houses (and protects) an inner substantially rigid and inflexible annular wall 122, and concentrically inwardly therein, an annular flexible wall 114 comprised of an air impervious material (such as silicone). The space between the walls 114 and 122 defines an airtight air chamber 108. Collectively, the walls 114 and 122, and the air chamber 108, define a bladder. A hose connection 148 allows for pneumatic communication between the bladder and an inflation pump and a deflation relief valve by means of air hose 148. An annular cavity 112 defined by the radially inwardly facing exterior surface 117 of the wall 114 is adapted to receive a finger 308 when the bladder is deflated. Annular rings 106 affixed to opposing sides of the cuff 102 retain the bladder therein.

The base 104 houses a pump 144 for controllably inflating the bladder via the air hose 148, a pressure sensor 140 for providing indications of bladder pressure applied to the finger, and a relief valve 142 for controllably deflating the bladder via the air hose 148. The base also houses a temperature sensor 120 (such as an infrared sensor, thermopile, or thermocouple) for measuring body temperature at the finger, and circuitry, including a microprocessor 146. The microprocessor is operatively coupled to/interfaced with the pump, the pressure sensor, relief valve and temperature sensor (and other sensors, switches and control devices disclosed herein) for receiving pressure sensor and temperature data, controllably operating the pump and relief valve, and calculating blood pressure and body temperature measurements, and, if desired pulse rate, using the algorithms described below in connection with FIGS. 10-14. A USB communications port and/or wireless communications circuitry (e.g., Bluetooth) 116 may be provided for facilitating firmware updates and/or for offloading data from the VSMD to another device, e.g., a smartphone, and/or an apparatus, such as a remote patient monitoring system (RPMS). A power button 118 may be provided for powering the device up/down and/or for commencing a blood pressure/temperature measuring cycle. A proximity sensor (not shown) may be employed to detect the presence of a finger in the cuff so as automatically commence a blood measurement cycle and/or prevent inflation of the cuff unless a finger has been disposed therein. The housing 110, rings 106, and base 104 may be comprised of molded thermoplastic materials. Measurement may be performed at either the base of an index finger, or the tip of an index finger. One or more of the above components may be situated in or on the cuff 102.

As shown by arrows 115, the rigid outer wall 122 causes the flexible inner wall 114 to displace radially inwardly when the bladder is inflated so as to substantially uniformly narrow the diameter of the cavity 112, as shown by 114'. When inflated to position 114', the radially inwardly facing exterior surface 117 of the wall 114' completely envelopes a finger disposed therein to restrict blood flow in the finger, in a manner similar to the operation of a blood pressure arm cuff, and so as to allow a blood pressure measurement via the finger.

As shown in FIGS. 3A and 3B, the surface 117 of the wall 114 has a continuous circular cross section or is otherwise configured so as to surround substantially the entirety of the portion of the finger inserted into cavity 112 even when inflated to position 114'. The surface 117 of the bladder is generally flat, i.e., there are preferably no protrusions from, indentations in, or other irregularities to the surface 117 of the bladder. In this manner, substantially the entire surface 117 of the bladder envelopes and contacts the finger when the bladder has been inflated sufficiently to capture the finger.

As a consequence of the structure of the cuff 110 described above, and the circuitry and algorithms described herein, there is no need to employ electromagnetic radiation (EMR) based measurement techniques, including laser based or other optical based measuring techniques (such as mDLS) that employ measurement of EMR reflection and/or transmission to measure blood pressure. In particular, the uniform manner in which surface 117 of the bladder substantially completely surrounds, and compresses the entirety of, the periphery of the finger, together with the use of the oscillometric method described herein to analyze pressure data, blood pressure and pulse rate can be measured with substantially greater accuracy than if the bladder only partially surrounds the periphery of the finger. Significantly, supplemental EMR based measurements that purport to improve the accuracy of blood pressure and pulse rate measurements are not needed.

The cuff may be fixedly and immovably attached to the base, as shown. However, the cuff may be movable, such as via a ball joint, to allow rotation of the cuff relative to the base, and/or may be detachable from the base e.g., via a snap mount, and may electrically connected to the circuitry in the base via an extendable cable or wireless communication.

As shown in FIG. 2, a display may be provided on the underside or bottom of the VSMD 100 for displaying systolic blood pressure 130, diastolic blood pressure 132, pulse rate 134 and/or temperature 136.

Figure 4:
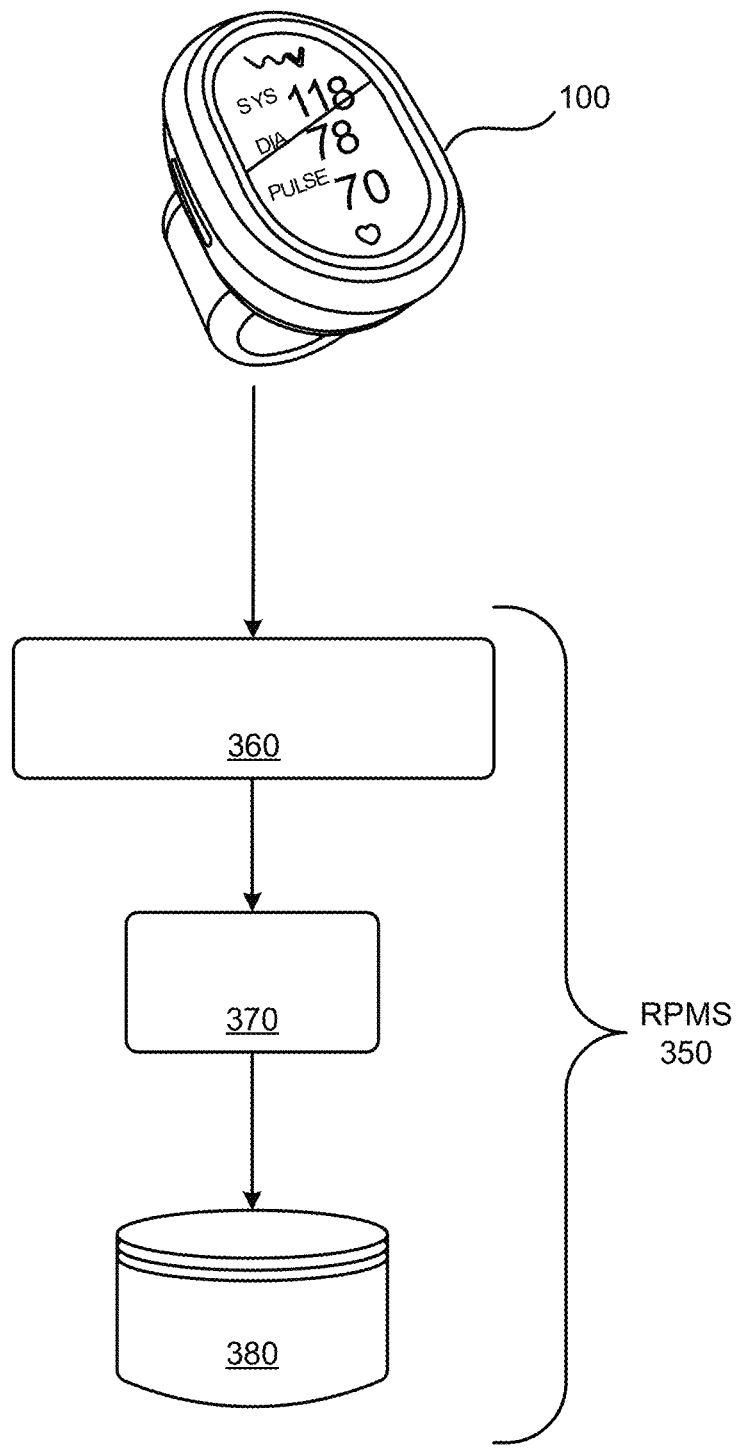
FIG. 4 illustrates a use case for the VSMD's disclosed herein, including those of FIGS. 1, 5 and 7.

FIG. 4 illustrates a use case of a VSMD that reports to a remote patient monitoring system (RPMS) 350. The RPMS comprises a connect module 360, a data aggregator 370 and a data store 380. The connect module 360 is configured to receive and accept connection attempts from a VSMD and to receive data from the VSMD. The data aggregator 370 determines the date/time of receipt of the data and causes the data to be stored in the data store 380. Examples of the data store 380 are an electronic medical record system (EMRS), electronic health records system (EHRS), and a clinical data repository (CDR).

The VSMD 100 may comprise software that prompts a user to connect her VSMD to a RPMS so that she can upload data from daily or nightly use of the VSMD. Communications between the VSMD and the user, the RPMS or others can include any one or more of text messages sent via a cell phone data network, emails sent via a cell phone data network, an audible alarm such as a beep from the VSMD, messages displayed on the display of the VSMD, and/or via haptics such as a buzzer or vibrator. For example, when the RPMS has not detected a communication from the VSMD and/or uploaded data therefrom for a period of time, the RPMS may send a communication such as an email, a text and/or a phone call to the user of the VSMD. The RPMS may be configured to self-initiate a communication with the VSMD for the purpose of transferring data from the VSMD to the RPMS. The VMSD may prompt the user of the VSMD for consent to upload data to the RPMS each time a transfer of data is initiated/requested by the RPMS.

Figure 5:
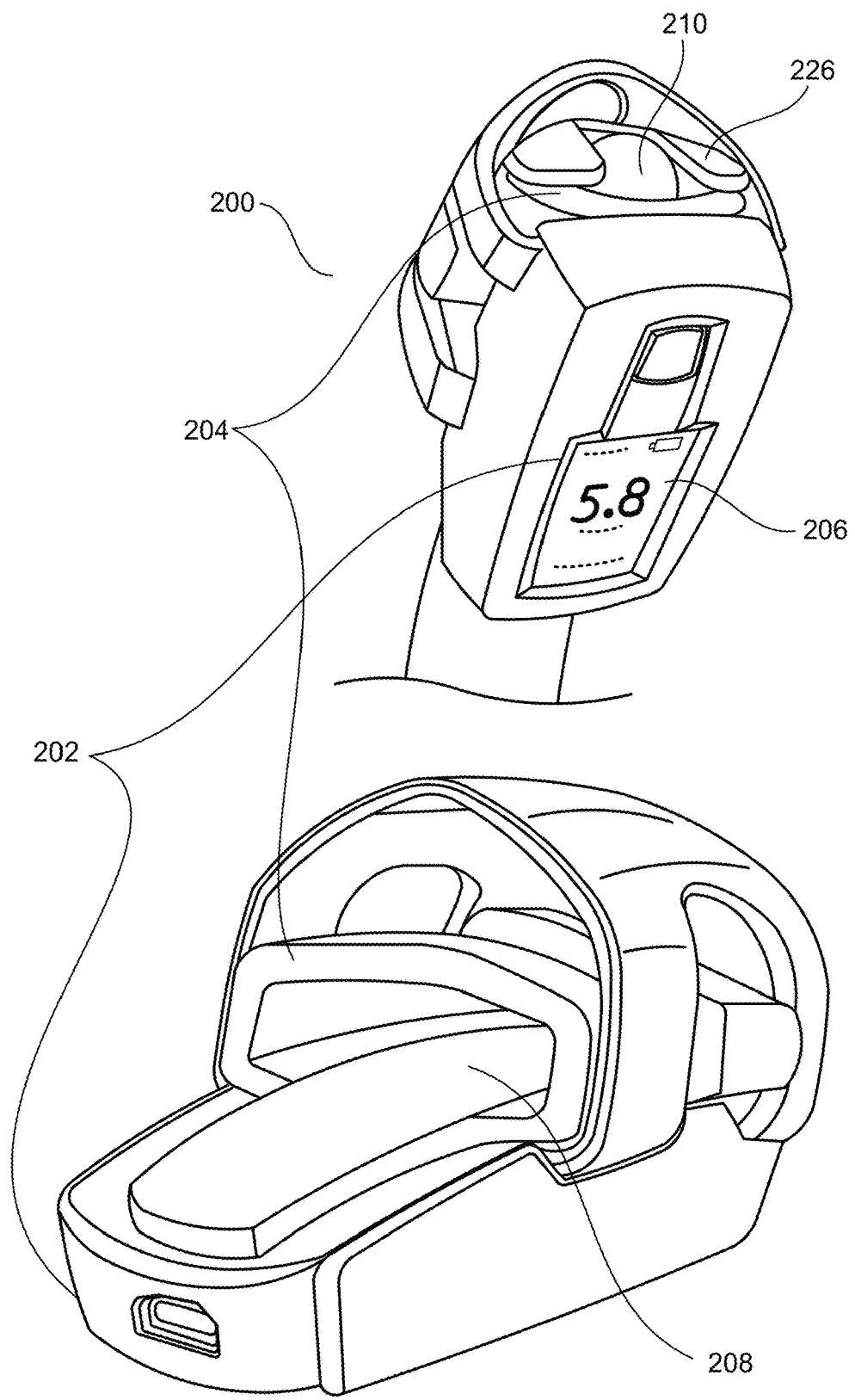
FIG. 5 illustrates a VSMD that include a physiological light monitoring system (PLMS) that employs light to measures vital signs, such as, but not limited to pulse rate, SPO2, hematocrit, total protein, blood glucose levels, respiratory rate, blood flow and/or EEG.
Figure 6A:
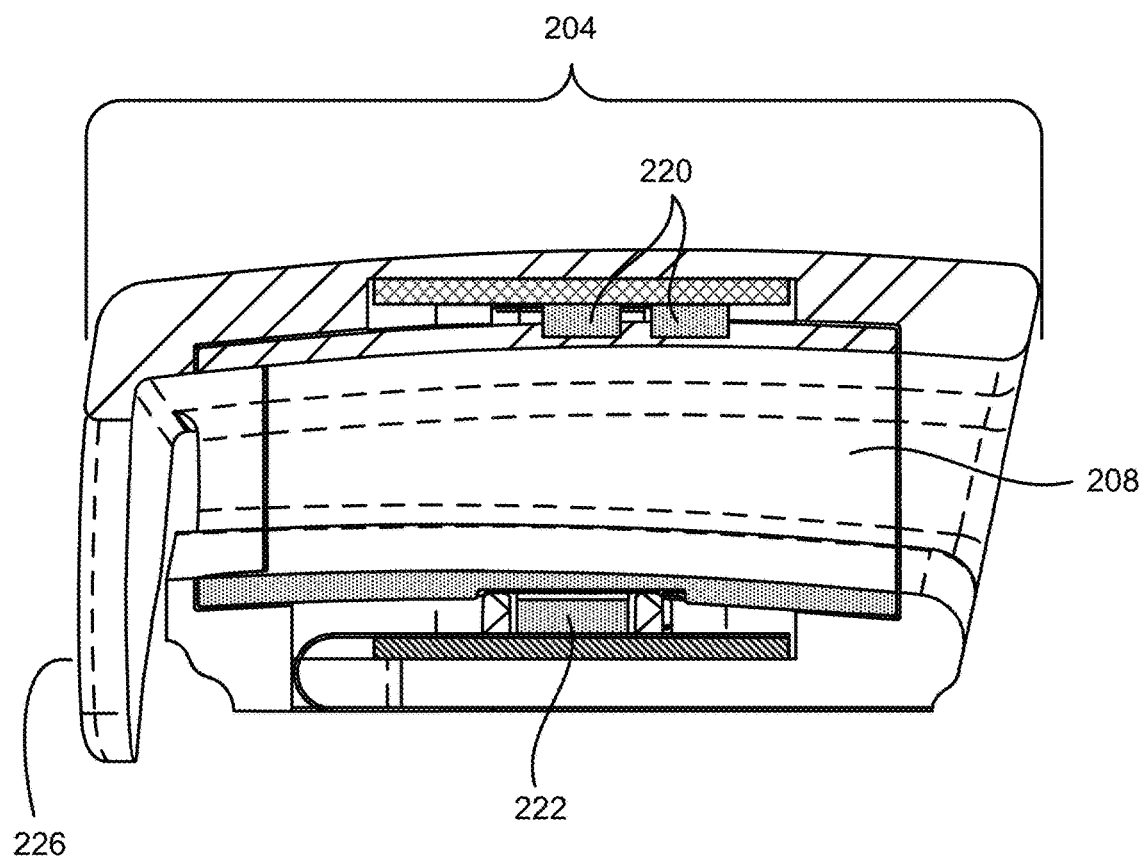
FIG. 6A is a cross section of the PLMS of FIG. 5 and illustrates the placement of light emitters and detectors for use in calculating vital sign data.
Figure 6B:
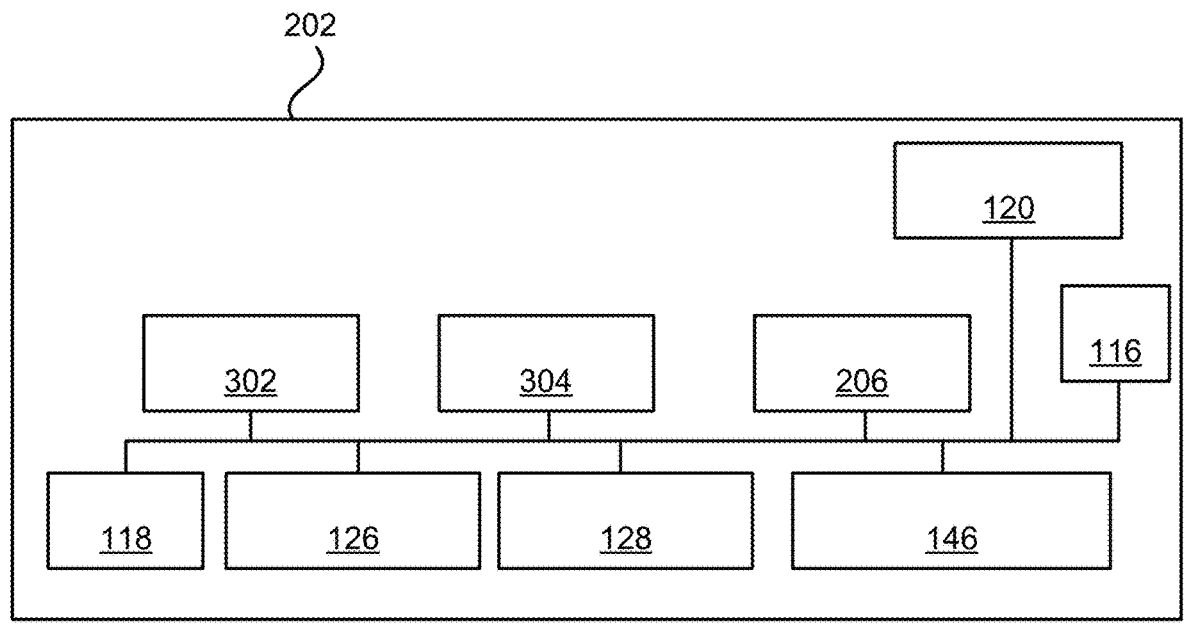
FIG. 6B is a block diagram of a base for the VSMD of FIG. 5 and illustrate various sensors, switches, and circuitry disposed therein.

FIGS. 5, 6A and 6B illustrate a VSMD 200 that employs light measurements to calculate vital signs and physiological characteristics such as blood glucose levels, respiration rate, saturation of peripheral oxygen (SpO2), blood flow, total hemoglobin (SpHb), pleth variability index (PVi), methemoglobin (SpMet), acoustic respiration rate (RRa), carboxyhemoglobin (SpCO), oxygen reserve index (ORi), oxygen content (SpOC), EEG, hematocrit (Hc) and total protein (TP). VSMD 200 comprises a base 202 and a physiological light monitoring subsystem (PLMS) 204. If desired, these light measurements may also be used to calculate heart rate, though not needed in view of the cuff structure and analytical methodologies described herein. The base includes a display 206 for displaying one or more of the vital signs/ physiological characteristics. Measurements are carried out after inserting one's finger 308 into the cavity 208 of the PLMS until the fingertip 210 reaches the fingertip stop 226. The References provide greater details as to how these measurements are carried out.

As shown in FIG. 6A, disposed within the PLMS are emitters 220 and emitter/detector 222 that emit/detect light as described below for obtaining data from which indications of these vital signs and physiological characteristics can be calculated. Emitters 220 and emitter/detector 222 are employed for transmissive light measurements (i.e., for measuring light emitted from emitters 220 and detected by emitter/detector 222 after being transmitted through a fingertip), whereas only emitter/detector 222 is employed for reflective light measurement (i.e., for emitting light, and measuring the light reflected from a fingertip).

Emitters 220 preferably emit light in two ranges: 640 nm-680 nm (and preferably at about 660 nm); and 920 nm to 960 nm (and preferably at about 940 nm). Emitter/ detector 222 preferably emits light in three ranges: 300 nm-415 nm (and preferably at about 395 nm); 640 nm-680 nm (and preferably at about 660 nm); and 920 nm-960 nm (and preferably at about 940 nm). Emitter/detector preferably detects light in the range of 200-1200 nm. Preferably, the photodiodes are physically arranged such that the emitters 220 are just above the fingernail and emitter/detectors 222 are just below the part of the bottom of the finger (the pad of the finger) under the fingernail. Further details are described in the References.

The VSMD 200 may also comprise a temperature sensor 120 for measuring body temperature at the finger, EKG pads 302, 304 for measuring EKG via one's fingertips, a camera module 126 for obtaining images of a portion of the skin of one's head when the VSM 200 is held adjacent the face, and a three-axis accelerometer 128 for detecting movement of the VSMD. The accelerometer may be used to terminate a respiratory rate measurement (or other measurement) upon detecting movement. The accelerator may also be employed for fitness tracking, e.g., measuring steps walked. A power switch 118 and a USB port 116 may also be provided. Each of these components may be disposed in the base 202 of the VSMD 200. The display 206 may be integrated into the base.

Figure 7:
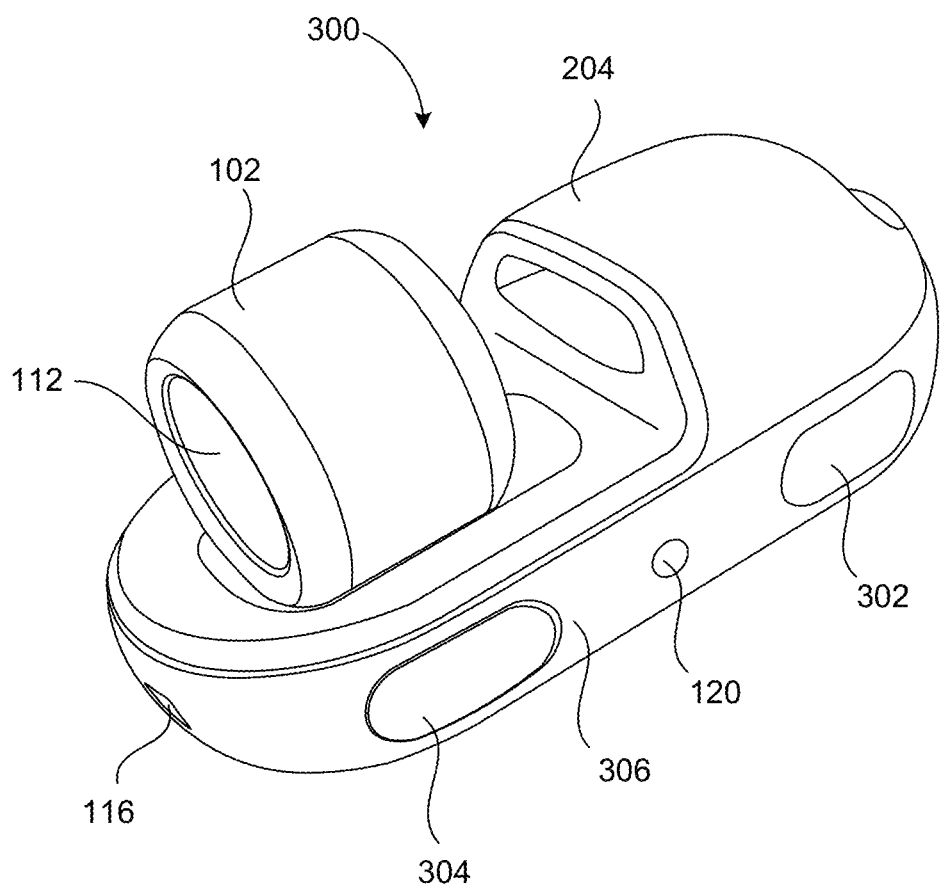
FIG. 7 is a perspective view of a VSMD for measuring multiple vital signs, including those measured by the VSMD of FIG. 1 and those measured by the VSMD of FIG. 5.
Figure 8:
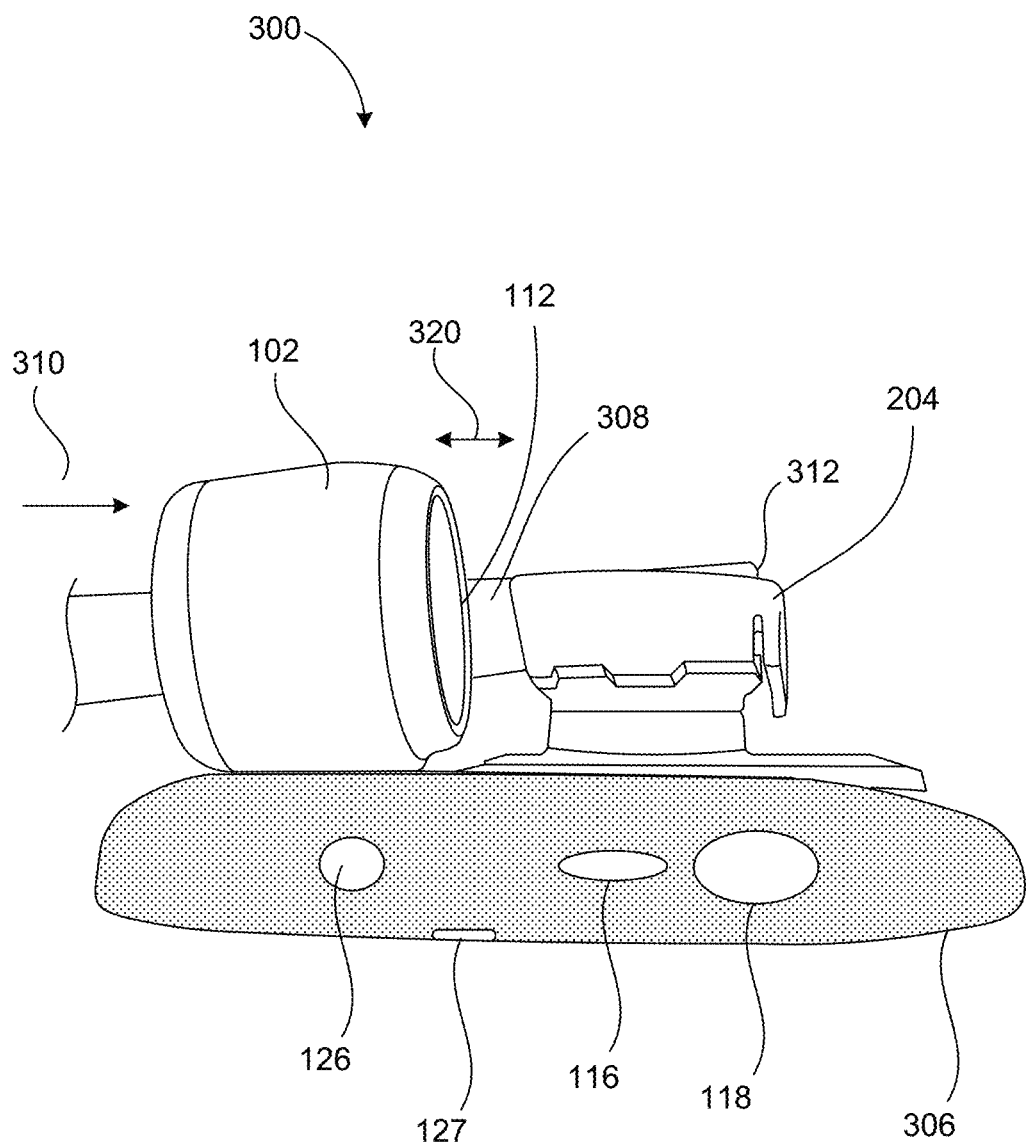
FIG. 8 is a side view of the VSMD of FIG. 7 and illustrates a finger therein.

FIGS. 7 and 8 illustrate a VSMD 300 for measuring all of the vital signs identified above in connection with FIGS. 1 and 5. That is, all of the aforementioned features may be combined into one device 300. As shown, the VSMD 300 includes a cuff 102 for measuring blood pressure, similar to that disclosed in connection with FIGS. 1-3, a PLMS 204 for measuring one or more of the other vital signs/physiological characteristics, similar to that disclosed in connection with FIGS. 5 and 6, and a base 306 for housing all of the components shown in the base 104 of VSMD 100 and base 202 of VSMD 200. The cuff 102 may be affixed to the base 306 as described above. As above, the base 306 may comprise a communications port 116 and a temperature sensor 120. The base may also house a pair of pads 302, 304 for measuring EKG. As shown by the arrow 320 in FIG. 8, the cuff may translate along a longitudinal axis of the base to facilitate insertion, in direction 310, of the base of the finger 308 into the cuff and of the fingertip 312 into the PLMS. As above, one or more of the pump, relief valve, pressure sensor, emitters, detector, communications port, power switch, camera, accelerometer and circuitry (including the microprocessor) may be housed inside the base 306. The VSMD 300 of FIGS. 7 and 8 may be considered as a combination of the VSMD 100 of FIGS. 1-3 and the VSMD 200 of FIGS. 5 and 6.

Disposed on the bottom or underside of the VSMD 300, there may be a stethoscope diaphragm 127 for detecting heart beats. The analog output of the diaphragm 127 may be digitized by an analog to digital converter, and the digital output thereof provided to the microprocessor 146 for processing to generate an indication of heart beats. Heartbeat data may be displayed on the VSMD or communicated for display, on. E.g., a smart phone. This structure defines a digital stethoscope that may be used by holding the bottom or underside of the VSMD against the user's chest, in the same manner as a traditional stethoscope.

Figure 9:
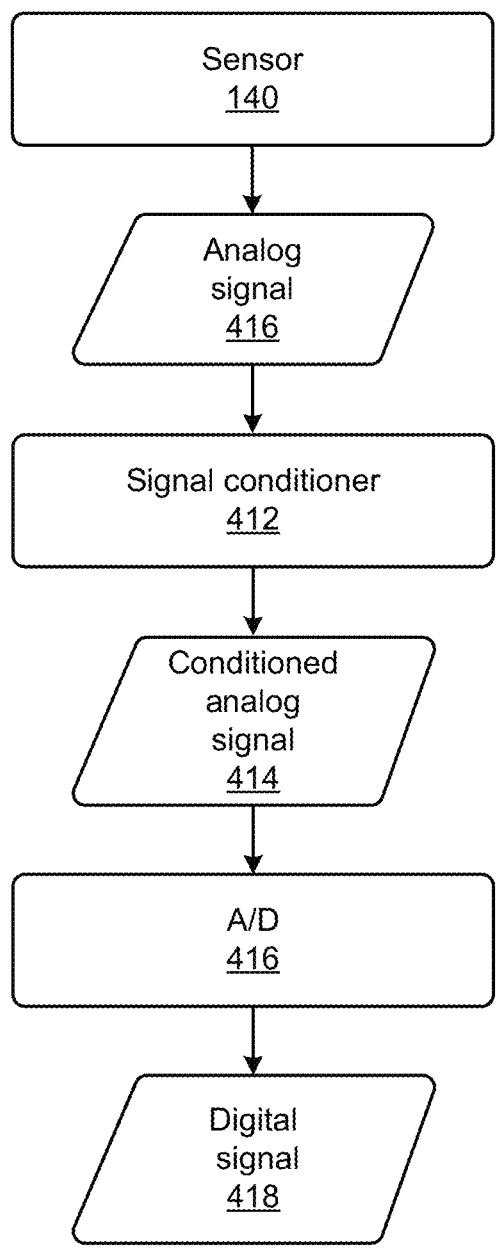
FIG. 9 is a block diagram of a system for obtaining digital pressure data from an analog pressure sensor disposed in a VSMD.
Figure 10:
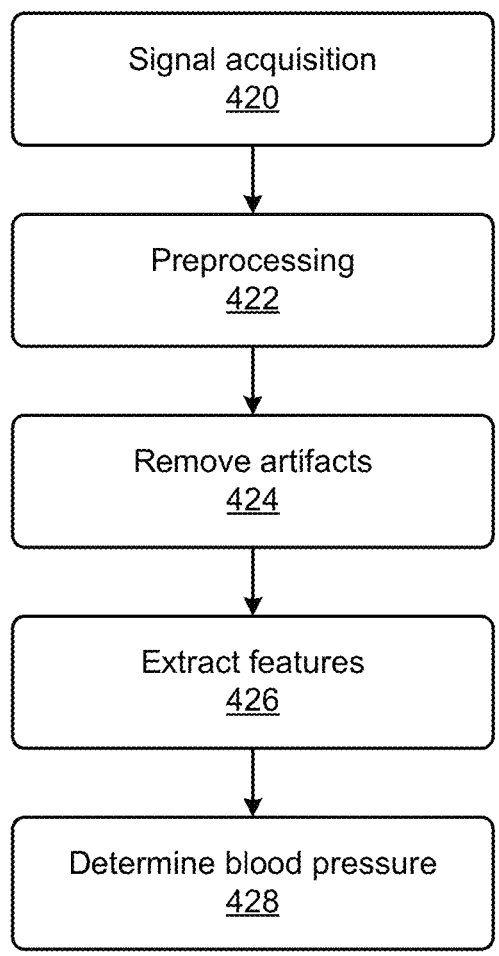
FIGS. 10-14 illustrate methods of processing the digital pressure sensor data to obtain blood pressure indications.

FIG. 9 illustrates a system for obtaining digital pressure data from the analog pressure sensor 140. The analog signal 410 from the pressure sensor is provided to a signal conditioner 412 that performs functions such as filtering and amplifying the analog pressure sensor signal and providing power to the sensor. The conditioned signal 414 is provided to an analog to digital converter 416, so as to provide digital pressure sensor data.

Referring to FIGS. 10-14, there is shown a method of determining blood pressure, i.e., systolic blood pressure (SBP) and diastolic blood pressure (DBP), pulse rate via the pressure sensor data. This method may be employed as a supplement of measuring other vital signs using the PLMS. SBP and DBP are derived, via the microprocessor 146, from the representations of a pulsatile oscillometric waveform (POW) in the digital pressure sensor data. The use of POW to derive blood pressure is known in connection with arm cuff blood pressure measuring devices.

Figure 16A:
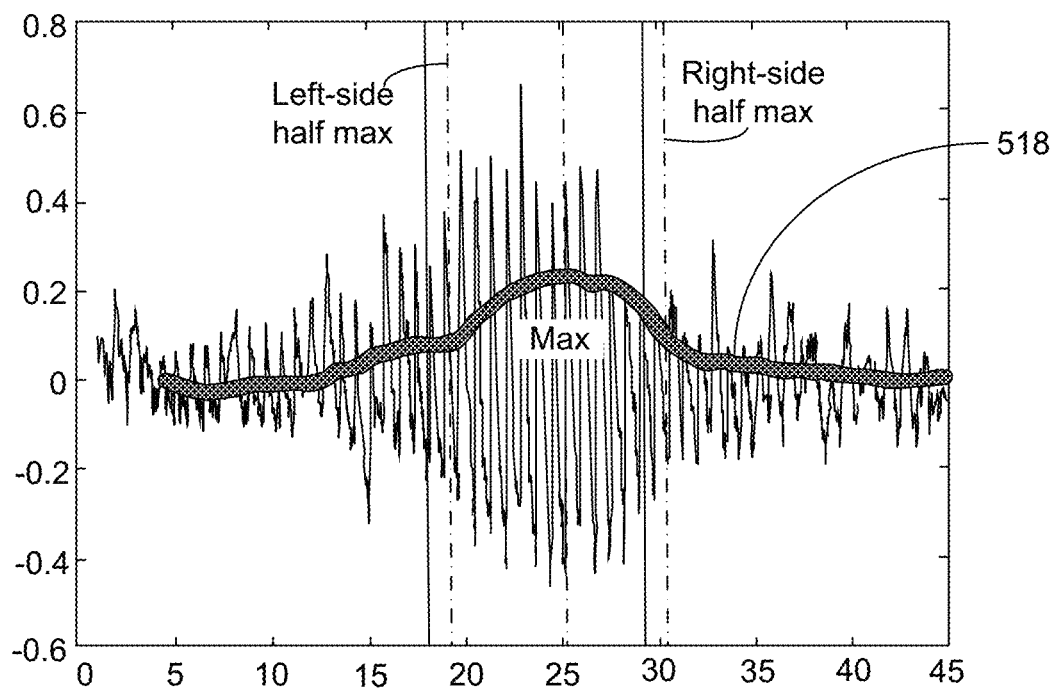
FIGS. 16A and 16B illustrate an oscillometric waveform and an oscillometric waveform envelope, respectively.
Figure 16B:
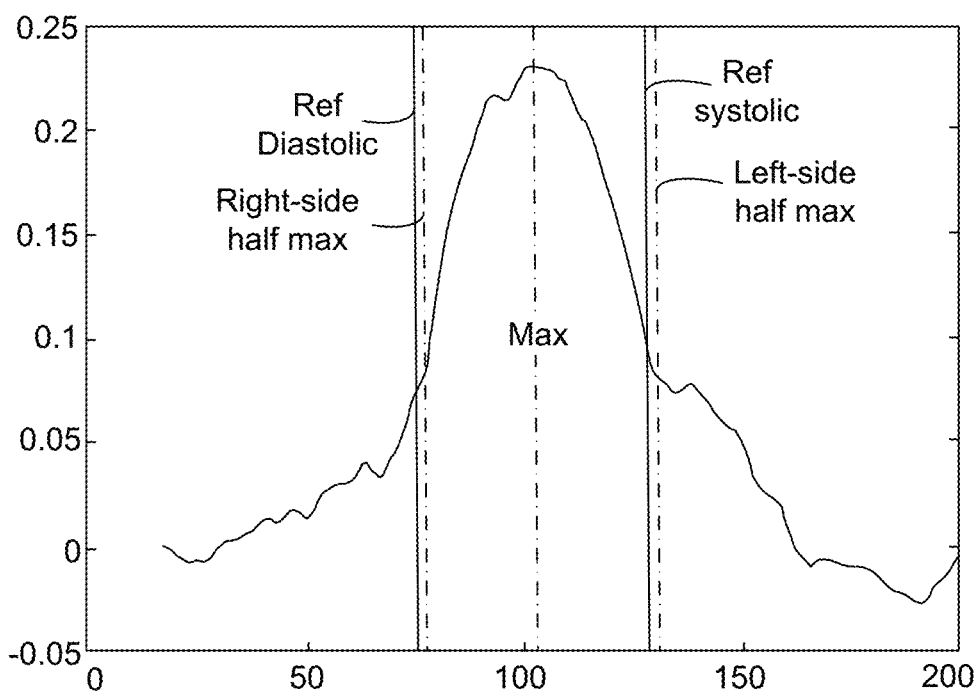
Figure 17:
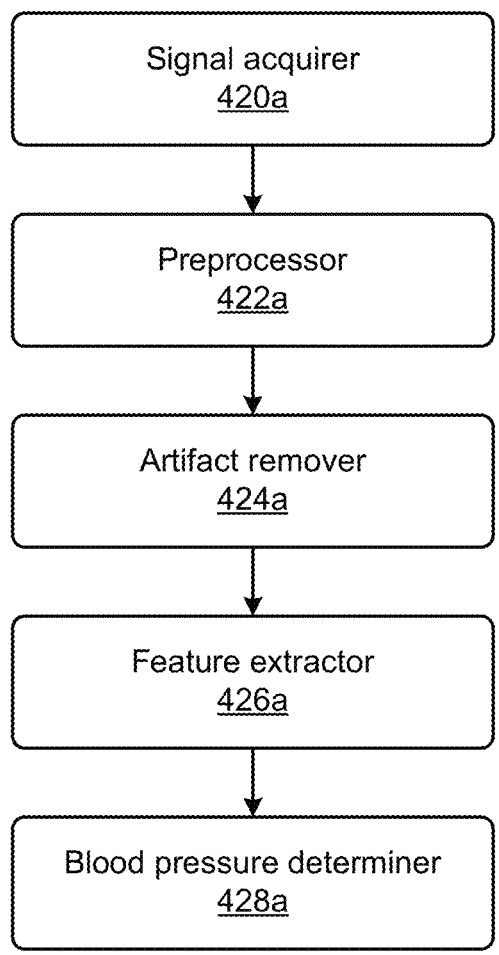
FIG. 17 is a block diagram of a blood pressure determiner.

FIG. 16A is one example of an oscillometric waveform vs time (seconds). FIG. 16B is one example of an oscillometric waveform envelope vs. pressure (mmHg). The fixed-ratio method is employed to estimate systolic and diastolic blood pressure values from this data. Digital pressure sensor data 418 is acquired (420) and then preprocessed (422) in the manner described in connection with FIG. 11. Artifacts are removed (424) so as to generate clean pressure sensor data, as described in connection with FIG. 12. Features are extracted from the cleaned pressure sensor data (426), as described in connection with FIG. 13. Thereafter, SBP and DBP are determined (428), as described in connection with FIG. 14. The method of FIG. 10 may be carried out by a blood pressure determiner—see FIG. 17, wherein the structural elements indicated by reference numerals 420a, 422a, 424a, 426a and 428a correspond respectively to the methods 420, 422, 4242, 426 and 428 of FIG. 10. The method of FIG. 10 may employ polling-driven acquisition of pressure data, applying a low pass filter to the pressure data to remove the pressure decrease ramp so as to create an oscillometric waveform, applying a root mean square averaging to the oscillometric waveform to create an oscillometric waveform envelope, and applying the fixed-ratio method to the oscillometric envelope to estimate systolic and diastolic blood pressure.

Figure 11:
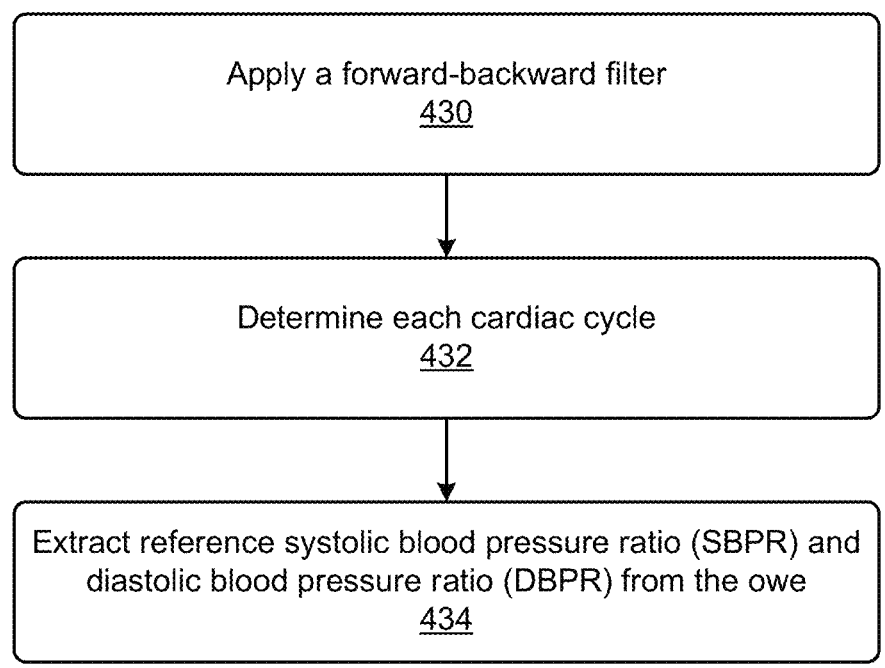

Referring to FIG. 11, there is shown one example of a method of preprocessing pressure sensor data. The method comprises applying a forward-backward filter to the acquired pressure sensor data (430) to obtain a zero-phase response, determining each cardiac cycle in reference to the intervals between two consecutive R-peaks in the EKG waveforms (432) and extracting reference systolic blood pressure ratio (SBPR) and diastolic blood pressure ratio (DBPR) from the oscillometric waveform envelope (OWE) (434). SBPR and DBPR are defined as follows: SBPR=SBPA/MA; DBPR=DBPA/MA, where MA represents the maximum amplitude of the OWE corresponding to the location of the mean arterial pressure (MAP), while SBPA and DBPA indicate the amplitudes of the OWE corresponding to the location of the SBP and the DBP respectively.

Figure 12:
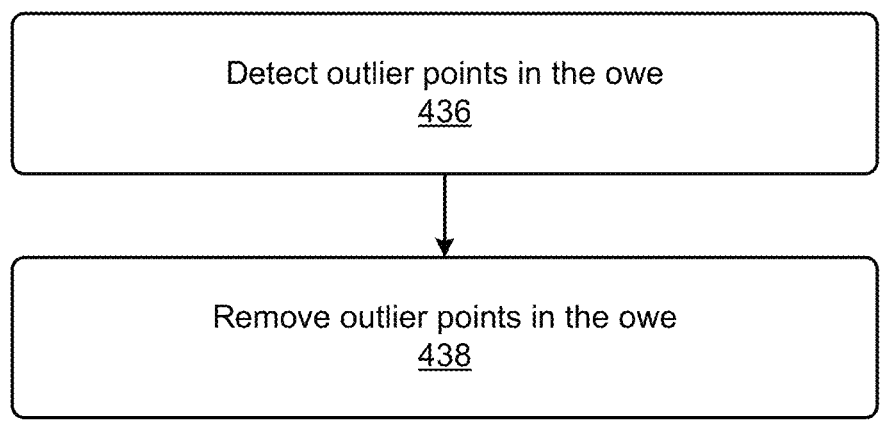

FIG. 12 illustrates one example of a method for removing artifacts (outlier points) from preprocessed pressure sensor data. The method comprises fitting a cubic spline curve to the OWE. To increase the accuracy of the SBP and DBP estimation, data points contaminated with motion artifact (motion discussed below) are treated as outliers and removed during the OWE curve fitting process. As shown at 436, the method includes detecting outlier points in the OWE based on the sudden increase of cuff pressure during deflation and the oscillometric pulses relative to their respective nearby pulses. Peak, peak-to-peak, peak-to-bottom and bottom points of the oscillometric pulses are analyzed. To be considered as clean data pulses, the absolute variations of the heights should not be more than 0.4 beats per minute and the height of each of these points should lie within ±50% of their respective nearby pulses based on modification of arterial volume pulsations and the elastogram. In addition, a sudden increase in pressure during cuff deflation will also be considered as artifact. Outlier points are then removed (438).

Figure 13:
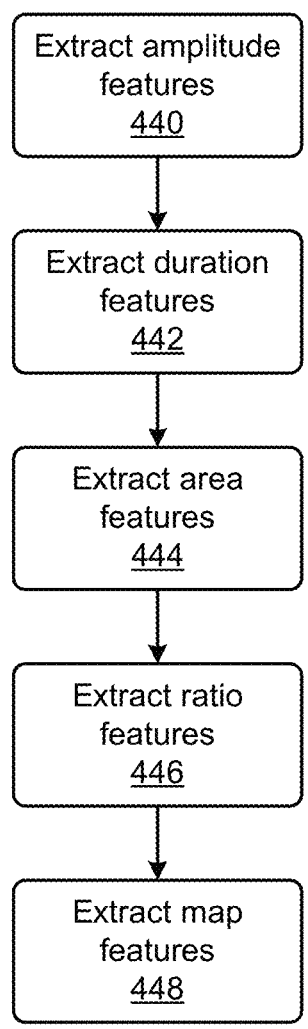

FIG. 13 illustrates one example of a method for extracting features from cleaned pressure sensor data. These features can be categorized in into five classes: (i) Amplitude; (i) Duration; (iii) Area; (iv) Ratio; and (v) MAP (estimated using the maximum amplitude process (MAA) approach). The method comprises extracting amplitude features (440), extracting duration features (442), extracting area features (444), extracting ratio features (446) and extracting MAP features (448).

The Duration class of features, (Dur1 and Dur2—see below), improve the SBP and DBP estimates using the relationships between the mean cuff pressure and pseudo envelopes of the cleaned pressure sensor data. The Area class of features (Area, Area2 and Area3—see below) is based on area measurements, and is based on the morphology of the OWE, which shows the dependence of the SBP and DBP estimates on the shape of the OWE.

In some cases, up to 6 features may be extracted from the OWE: maximum amplitude (MA) of OWE (Amp1); duration for MA to occur (Dur1); duration of OWE (Dur2); area under OWE (Area1); duration for maximum amplitude to occur/duration of OWE (Ratio1) and MAP estimated using the MAA algorithm. In other cases, up to 10 features may be extracted from the OWE: Amp1; Dur1; Dur2; Area1; area under OWE before the MA's position (Area2); area under OWE after the MA's position (Area3); Ratio1; area under OWE before the MA's position/area under OWE (Ratio2); area under OWE after the MA's position/area under the OWE (Ratio3); and, MAP estimated using the MAA algorithm.

Figure 14:
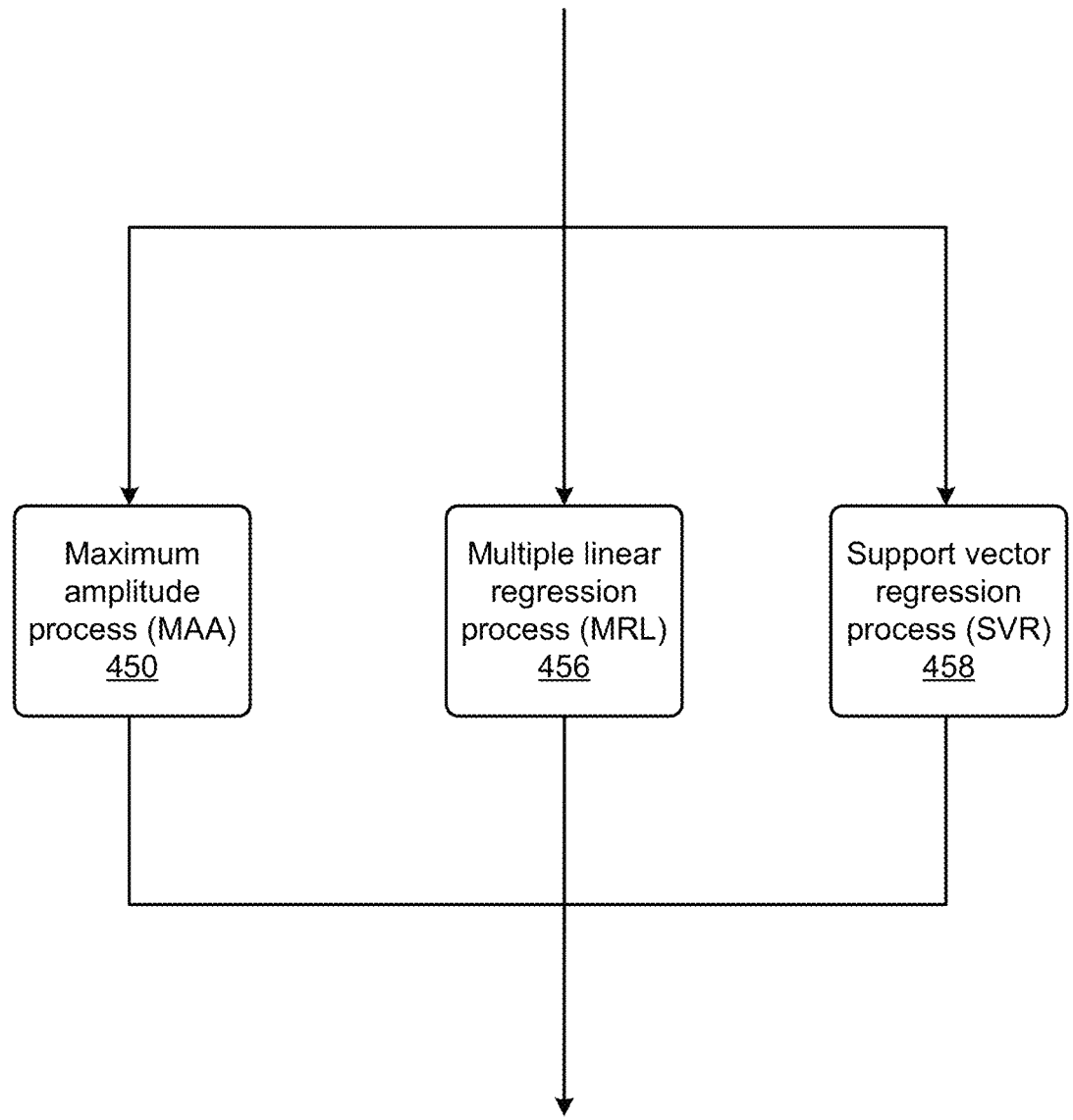

FIG. 14 illustrates a method of determining blood pressure from features of blood pressure data. Examples of processes for determining blood pressure from features of blood pressure data include but are not limited to the MAA method based on the fixed characteristic ratio (450); a multiple linear regression process (MLR) (456); and, a support vector regression process (SVR) (458).

Figure 15:
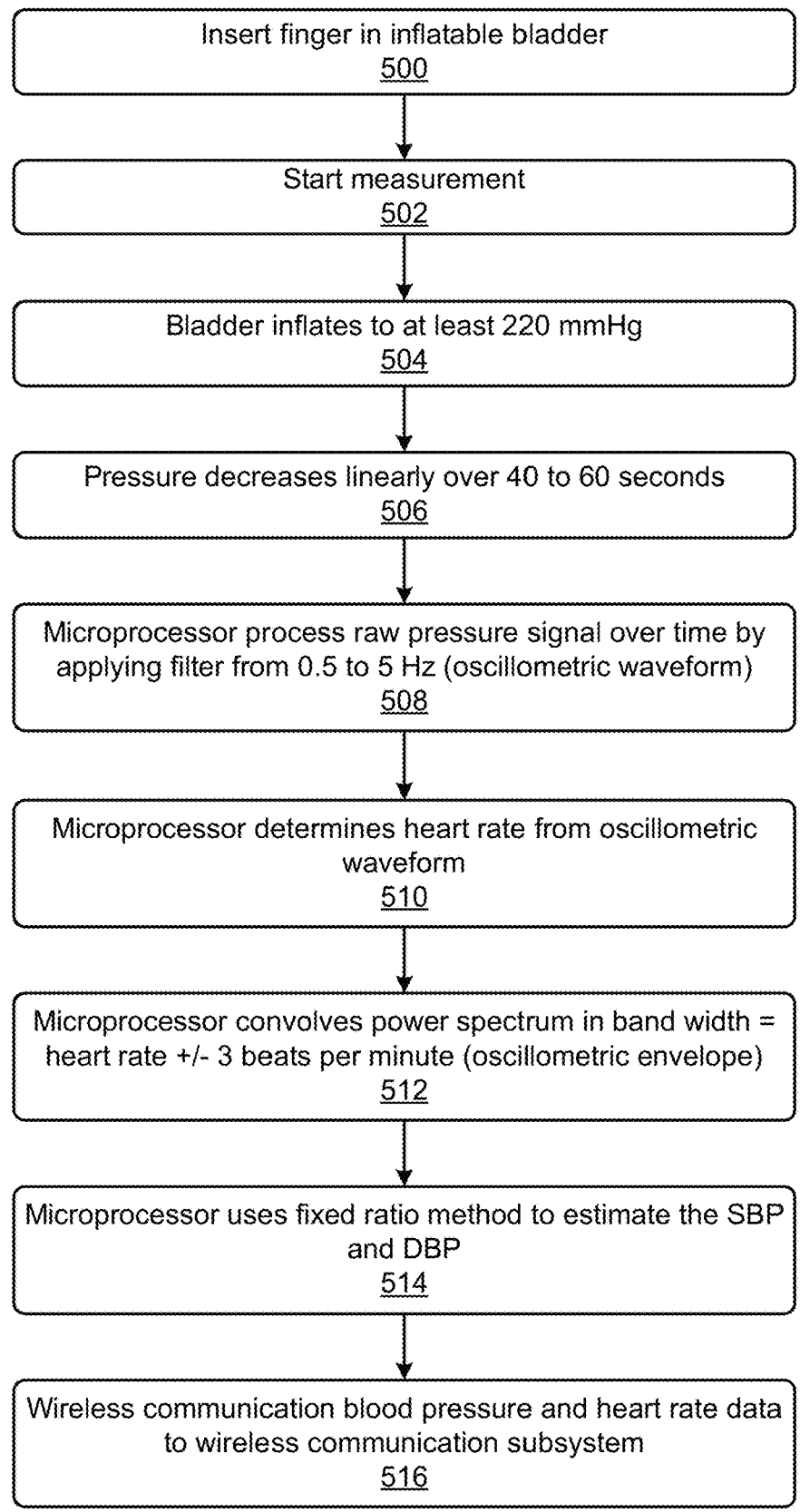
FIG. 15 is a flowchart illustrating further details of a process for determining and communicating blood pressure data.

FIG. 15 illustrates a method for determining and communicating blood pressure data. After a finger has been inserted into the cavity 112 of the bladder (500), measurements may begin (502). Once a measurement cycle has begun, the pump inflates the bladder to a target pressure, which is generally at least 220 mmHg (504). Once the bladder has reached its target pressure, the relief valve is controllably opened to allow the bladder pressure to decrease in a linear fashion over a period of 40-60 seconds (506). All of the foregoing steps are carried out under control of the microprocessor 146 executing appropriate program code. As the bladder is deflated, the microprocessor processes raw pressure signal data over a period of time by applying a 0.5 Hz to 5 Hz filter thereto, to yield the oscillometric waveform (508). The oscillometric waveform data is analyzed by the microprocessor to provide an indication of heart rate (510). Heart rate data is then processed by the microprocessor to create a power spectrum 518 (FIG. 16A), and the microprocessor then convolves the power spectrum as noted at 512. The microprocessor then employs the fixed ratio method to provide an indication of SBP and DBP (514). Blood pressure and heart rate data is then communicated to a subsystem for storage and later use, either within the VSMS or remote from the VSMD, e.g., the RPMS (516).

Figure 18:
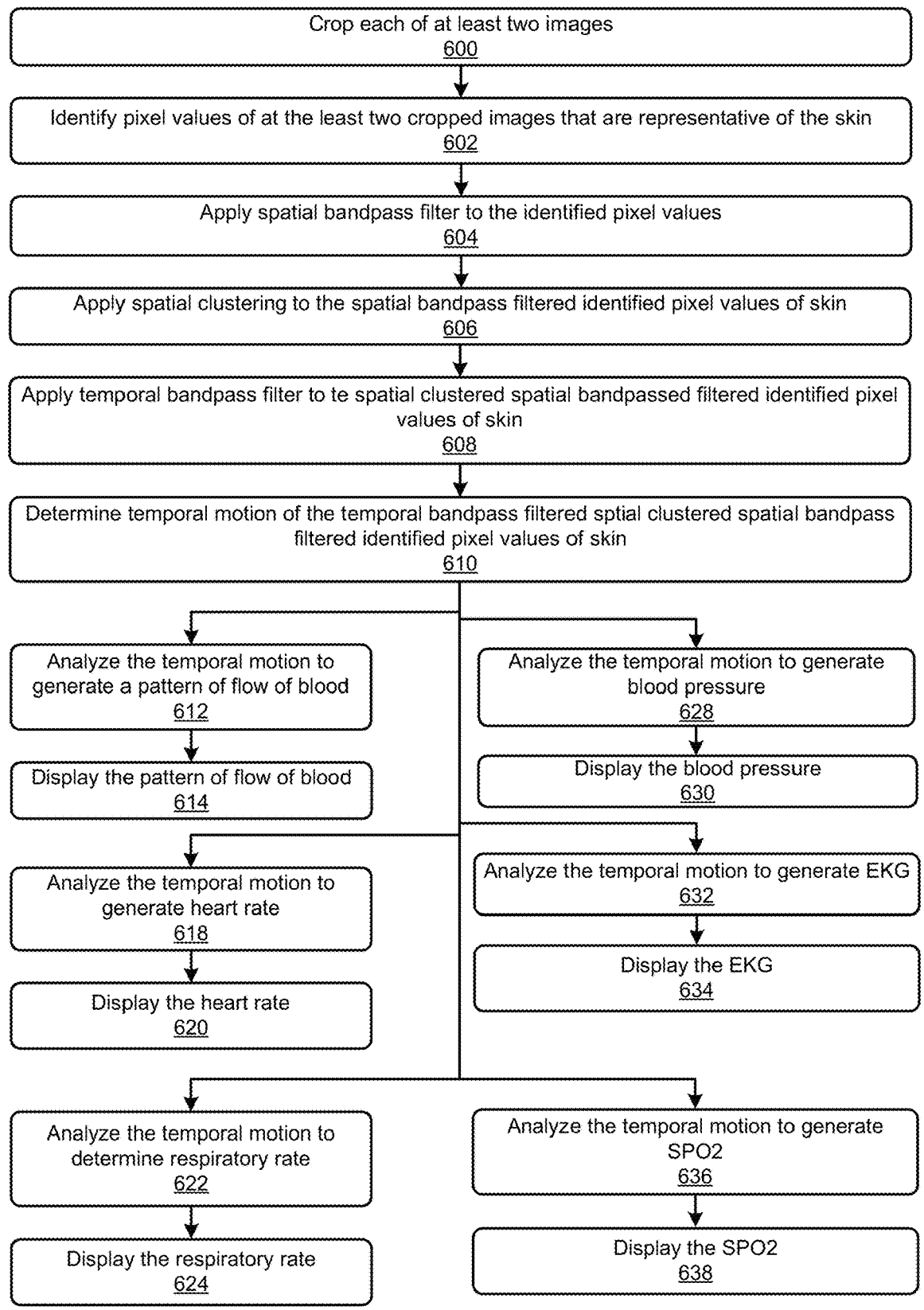
FIG. 18 is a flowchart illustrating a method of motion amplification from which to generate and communicate vital signs.

FIG. 18 illustrates an alternative (and/or supplemental) method of obtaining indications of blood pressure and heart rate, as well as other vital signs such as blood flow, respiratory rate, EKG, and SpO2 via camera images. The method of FIG. 18 analyzes the temporal and spatial motion in digital images of a subject to obtain an indication of these vital signs. Particularly, the method analyzes temporal motion of cropped images representative of a portion of the skin of a user's face, as taken by the camera 126. The References provide further details.

The method comprises cropping a plurality of images from the camera to exclude areas that do not include a skin region (600). For example, the excluded area can be a perimeter area around the center of each image, so that an outside border area of the image is excluded. For example, about 72% of the width and about 72% of the height of each image may be cropped, leaving about 7.8% of the original image. This action eliminates about $^{11}/_{12}$ of each image and reduces the amount of processing time needed to carry out the remainder of the method. After cropping, the remaining image may be a square or circular area. A cropper module may be employed to carry out step 600.

Pixel-values of the cropped images may identify areas that are representative of the skin (602). An automatic seed point-based clustering process may be applied to at least two images. A spatial bandpass filter, such as a two-dimensional spatial Fourier Transform, a high pass filter, a low pass filter, a bandpass filter, or a weighted bandpass filter, may be applied to the identified pixel-values (604). At 606, spatial clustering, such as fuzzy clustering, k-means clustering, an expectation-maximization process, Ward's method or seed point-based clustering, is applied to the spatial bandpass filtered identified pixel-values of skin. A temporal bandpass filter, such as a one-dimensional spatial Fourier Transform, a high pass filter, a low pass filter, a bandpass filter or a weighted bandpass filter, is applied to the spatial clustered spatial bandpass filtered identified pixel-values of skin (608). Temporal motion of the temporal bandpass filtered, spatial clustered spatial bandpass filtered, identified pixel-values of skin is determined (610).

A pattern of blood flow may be determined by analyzing the temporal motion, such as by analyzing motion changes in the pixels and the temporal motion of color changes in the skin (612) and is displayed (614).

Heart rate may be determined by analyzing the temporal motion, for example by analyzing the frequency spectrum of the temporal motion in a frequency range for heart beats, such as 0 hz-10 Hz (618) and displayed (620).

Respiratory rate may be determined by analyzing the temporal motion to determine respiratory rate, such as by analyzing the motion of the pixels in a frequency range for respiration, such as 0 Hz-5 Hz (622) and displayed (624).

Blood pressure may be determined by analyzing the temporal motion, such as by analyzing the motion of the pixels and the color changes based on the clustering process and potentially temporal data from the infrared sensor (628) and displayed (630).

EKG may be determined by analyzing the temporal motion (632) and displayed (634).

SpO2 may be determined by analyzing the temporal color changes, in conjunction with the k-means clustering process and potentially temporal data from the infrared sensor (636) and displayed (638).

Table 1 shows eight measurement implementations of the PLMS. In each case, transmissive EMR is read by emitting an amount of EMR at a specific wavelength and detecting an amount of the EMR at the specific wavelength (or within a range such as the specific wavelength ±20 nm) that passes through the user's finger. Reflective EMR is read by emitting an amount of EMR at a specific wavelength and then detecting an amount of the EMR at that specific wavelength (or within a range of wavelengths) that is reflected by the subject's finger. Measurements of EMR at 395 nm are performed to determine the amount of nitric oxide (NO) in the subject as a proxy for the amount of glucose in the subject. Measurements of EMR at 660 nm are performed to determine the amount of oxygen in the subject. Measurements of ER at 940 nm are performed as a baseline reference that is not affected by oxygen or nitric oxide. The References provide further details.

Implementation no. 1, measurement of transmissive SpO2, reflective SpO2 and reflective glucose: transmissive SpO2 is determined by reading transmissive EMR at 660 nm and transmissive EMR at 940 nm and dividing the amount of transmissive EMR at 660 nm by the amount of transmissive EMR at 940 nm. Reflective SpO2 is determined by reading reflective EMR at 660 nm and reflective EMR at 940 nm and dividing the amount of reflective EMR at 660 nm and by the amount of reflective EMR at 940 nm. Reflective glucose is determined by reading reflective EMR at 395 nm and reflective EMR at 940 nm and dividing the amount of reflective EMR at 395 nm by the amount of reflective EMR at 940 nm.

Implementation no. 2, measurement of transmissive SpO2 only, as indicated in implementation no. 1.

Implementation no. 3, measurement of reflective SpO2 only, as indicated in implementation no. 1.

Implementation no. 4, measurement of reflective glucose only, as indicated in implementation no. 1.

Implementation no. 5, measurement of reflective SpO2 and reflective glucose only, as indicated in implementation no. 1.

Implementation no. 6, measurement of reflective SpO2 and transmissive SpO2 only, as indicated in implementation no. 1.

Implementation no. 8, measurement of transmissive cellular only: measurement of transmissive cellular only the size of the red blood cells can be calculated using the ratio of transmissive 808 nm or 940 nm to transmissive 980 nm.

TABLE 1

| IMPLEMENTATON | DETERMINATION(S) | DETECT(S) | READING(S) |
|---|---|---|---|
| 1 | transmissive SpO2 | transmissive 660 nm/transmissive 940 nm | a) reflective 395 nm |

TABLE 1-continued

| IMPLEMENTATON | DETERMINATION(S) | DETECT(S) | READING(S) |
|---|---|---|---|
| | reflective SpO2<br>reflective glucose | reflective 660 nm/reflective 940 nm<br>reflective 395 nm/reflective 940 nm | b) transmissive 660 nm<br>c) reflective 660 nm<br>d) transmissive 940 nm<br>e) reflective 940 nm |
| 2 | transmissive SpO2 only | transmissive 660 nm/transmissive 940 nm | a) transmissive 660 nm<br>b) transmissive 940 nm |
| 3 | reflective SpO2 only | reflective 660 nm/reflective 940 nm | a) reflective 660 nm<br>b) reflective 940 nm |
| 4 | reflective glucose only | reflective 395 nm/reflective 940 nm | a) reflective 395 nm<br>b) reflective 940 nm |
| 5 | reflective SpO2<br>reflective glucose | reflective 660 nm/reflective 940 nm<br>reflective 395 nm/reflective 940 nm | a) reflective 395 nm<br>b) reflective 660 nm<br>c) reflective 940 nm |
| 6 | transmissive SpO2<br>reflective glucose | transmissive 660 nm/transmissive 940 nm<br>reflective 395 nm/reflective 940 nm | a) reflective 395 nm<br>b) transmissive 660 nm<br>c) transmissive 940 nm<br>d) reflective 940 nm |
| 7 | transmissive SpO2<br>reflective SpO2 | transmissive 660/transmissive 940 nm<br>reflective 660/reflective 940 nm | a) transmissive 660 nm<br>b) reflective 660 nm<br>c) transmissive 940 nm<br>d) reflective 940 nm |
| 8 | transmissive cellular only | transmissive 808 nm or 980 nm/transmissive 940 nm | transmissive 808 or 980 nm |

Implementations that employ a transmissive technique configuration (implementation nos. 1, 2, 6, 7 and 8) are believed to provide more accurate results than those that use only a reflective technique (implementation nos. 3, 4 and 5). It is believed that transmissive techniques provide greater accuracy because the amount of signal transmitted through the finger is greater than the amount of reflected signal, thus providing a stronger detected signal. Assuming the same signal strength for transmitted signals in the transmissive techniques and reflected signals in the reflective techniques, and the same background EMR noise, the transmissive techniques result in a higher signal-to-noise ratio.

As mentioned, the PLMS embodiments described herein are capable of measuring one or more of the following vital signs: blood glucose levels, heart rate, heart rate $$R_Y = \frac{\log\left(\frac{I_{AC} + I_{DC}}{I_{DC}}\right)_{Y\,[nm]}}{\log\left(\frac{I_{AC} + I_{DC}}{I_{DC}}\right)_{940\,[nm]}}$$

a. where:

b. $Y = \{660\,[nm], 395\,[nm]\}$ c. $I_{AC}$ is the frequency component of the Intensity signal d. $I_{DC}$ refers to the baseline component e. The relationship between $R_Y$ and the parameters, $P$, below is a general transfer function $T(R_Y)$, where:

-continued $$Z_N = \begin{Bmatrix} SpO2 \\ \text{total hemoglobin } (SpHb) \\ PVi \\ \text{methemoglobin}\,(SpMet) \\ \text{acoustic respiration rate } (RRa) \\ \text{carboxyhemoglobin}\,(SpCO) \\ \text{oxygen reserve index } (ORi) \\ \text{oxygen content } (SpOC) \\ \text{total protein } (TP) \end{Bmatrix}$$

where:
H is the hematocrit value (Hc);
ƒw is the tissue water fraction;
ƒpp is the plasma protein fraction;
R is the ratio of magnitudes of the blood pulse spectrum;
$\mu aHb(\lambda 1)$ is the sum of the absorption coefficient of the two forms of hemoglobin at a first wavelength;
$\mu aw(\lambda 2)$ is the absorption coefficient of water at a second wavelength;
$\Delta\mu s(\lambda 1)$ is the difference between the scattering coefficients of the blood and surrounding tissue at a first wavelength;
$\Delta\mu s(\lambda 2)$ is the difference between the scattering coefficients of the blood and surrounding tissue at a second wavelength; and
0.34 is the fraction of the red cell volume occupied by hemoglobin, which is assumed to be constant.
$Z_N = T_N(R_{660}, R_{395})$ (Z being the vital sign in the parentheses above and N being the ith component, e.g., $Z_1 = SpO2$, $Z_3 = PVi$)

In the embodiments of FIGS. 6-8, transmissive/transmissive or reflective/reflective measurements are performed. In implementation nos. 1 and 4-6 in Table 1, and in the embodiments of FIGS. 9 and 10, nitric oxide measurements are performed as a proxy for glucose, and are reflective measurements, because the 395 nm EMR emission is visible light that is not fully transmitted through a human finger.

Referring to the PLMS 204, the emitter 220 emits EMR at 395 nm, 660 nm and 940 nm, 220 and detector 222 detects EMR in the ranges of 300-415 nm, 640-680 nm and 920-960 nm, so as to measure reflected EMR in the wavelengths noted in Table 1. The PLMS may also determine near cellular sized features, as shown in implementation no. 8. In such case, the PLMS may include an emitter that emits EMR in the ranges of 808 nm or 980, so as to transmit EMR through the user's finger positioned within the PLMS. The detector may detect emitted EMR in the range of 1000 nm to 1800 nm. The microprocessor carries out the calculations noted above.

Further details for implementing circuitry and algorithms for each of the implementations can be found in the References.

Figure 19:
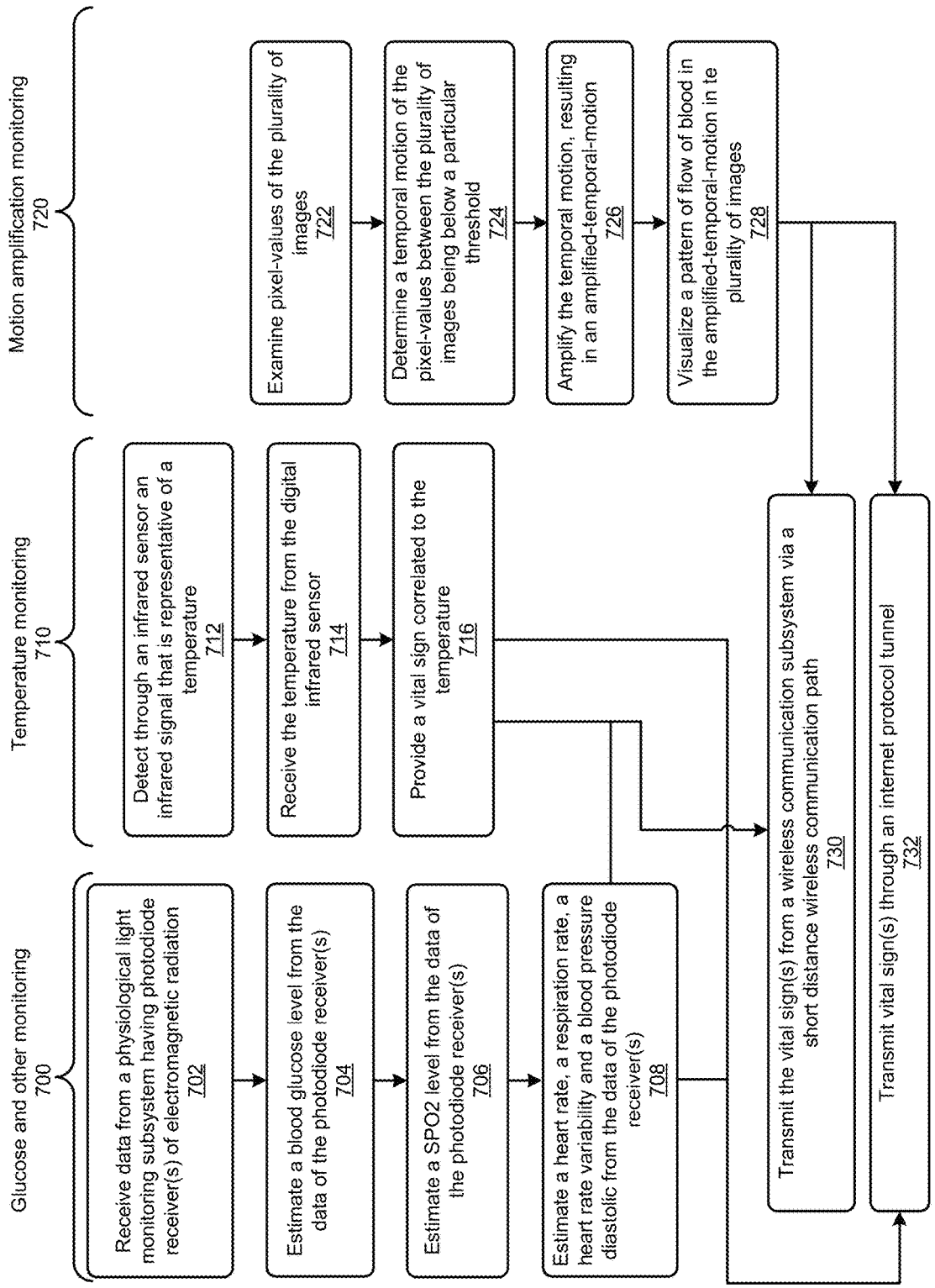
FIG. 19 illustrates methods for measuring glucose and other physiological characteristics such temperature, and details of temporal motion amplification.

FIG. 19 illustrates methods for measuring glucose (700) and other physiological characteristics such temperature (710) and provides additional details of temporal motion amplification (720) described above. However, the instant disclosure employs the method 700 (blocks 702-708), and other methods described herein and in the References, to measure TP and Hc.

Referring to method 700, methods of measuring blood glucose and other physiological characteristics/vital signs include receiving data from a SpO2/glucose subsystem having photodiode receivers of ER (702). One example of the SpO2/glucose subsystem is PLMS 204. Blood glucose levels and SpO2 can be derived via the data received from the detector 222 (704, 706). Heart rate, respiration rate, heart rate variability and DBP may also be derived (708).

Measurement of Hc and TP may also employ the PLMS and an alternate version of method 700. In this case, data from a reflective 395 nm emitter is used to calculate TP via a ratio with data from a reflective 940 nm emitter on side of the finger opposite the fingernail. The hematocrit is calculated via the transmissive 660 nm and 940 nm signals via the equation below where $f_w$ and $f_{pp}$ are parameters established through clinical trial calibration with the patients.

$$\frac{1}{H} \cong \frac{0.34}{1 - f_w - f_{pp}} \left( 1 + R \frac{\mu_a^{Hb}(\lambda_1) + \Delta\mu_s(\lambda_1)}{\mu_a^w(\lambda_2) + \Delta\mu_s(\lambda_2)} \right)$$

where:
H is the hematocrit value (Hc);
fw is the tissue water fraction;
fpp is the plasma protein fraction;
R is the ratio of magnitudes of the blood pulse spectrum;
μaHb(λ1) is the sum of the absorption coefficient of the two forms of hemoglobin at a first wavelength;
μaw(λ2) is the absorption coefficient of water at a second wavelength;
Δμs(λ1) is the difference between the scattering coefficients of the blood and surrounding tissue at a first wavelength;
μps(λ2) is the difference between the scattering coefficients of the blood and surrounding tissue at a second wavelength; and
0.34 is the fraction of the red cell volume occupied by hemoglobin, which is assumed to be constant. p
Method 710 may include detecting through the infrared sensor (e.g., 120) an infrared signal that is representative of a body surface temperature (712), receiving the body surface temperature from the infrared sensor (714), and providing a data such as body core temperature correlated to the body surface temperature (716).

Method 720 may include examining pixel values of a plurality of images (722) of the finger, determining a temporal motion of the pixel values between the plurality of images being below a particular threshold (724), amplifying the temporal motion, resulting in an amplified temporal motion (726), and visualizing a pattern of flow of blood in the amplified temporal motion in the plurality of images (728).

The measured vital signs may be transmitted from a communication subsystem, e.g., via a short distance wireless communication path (730), and/or securely to a RPMS (732).

Figure 20:
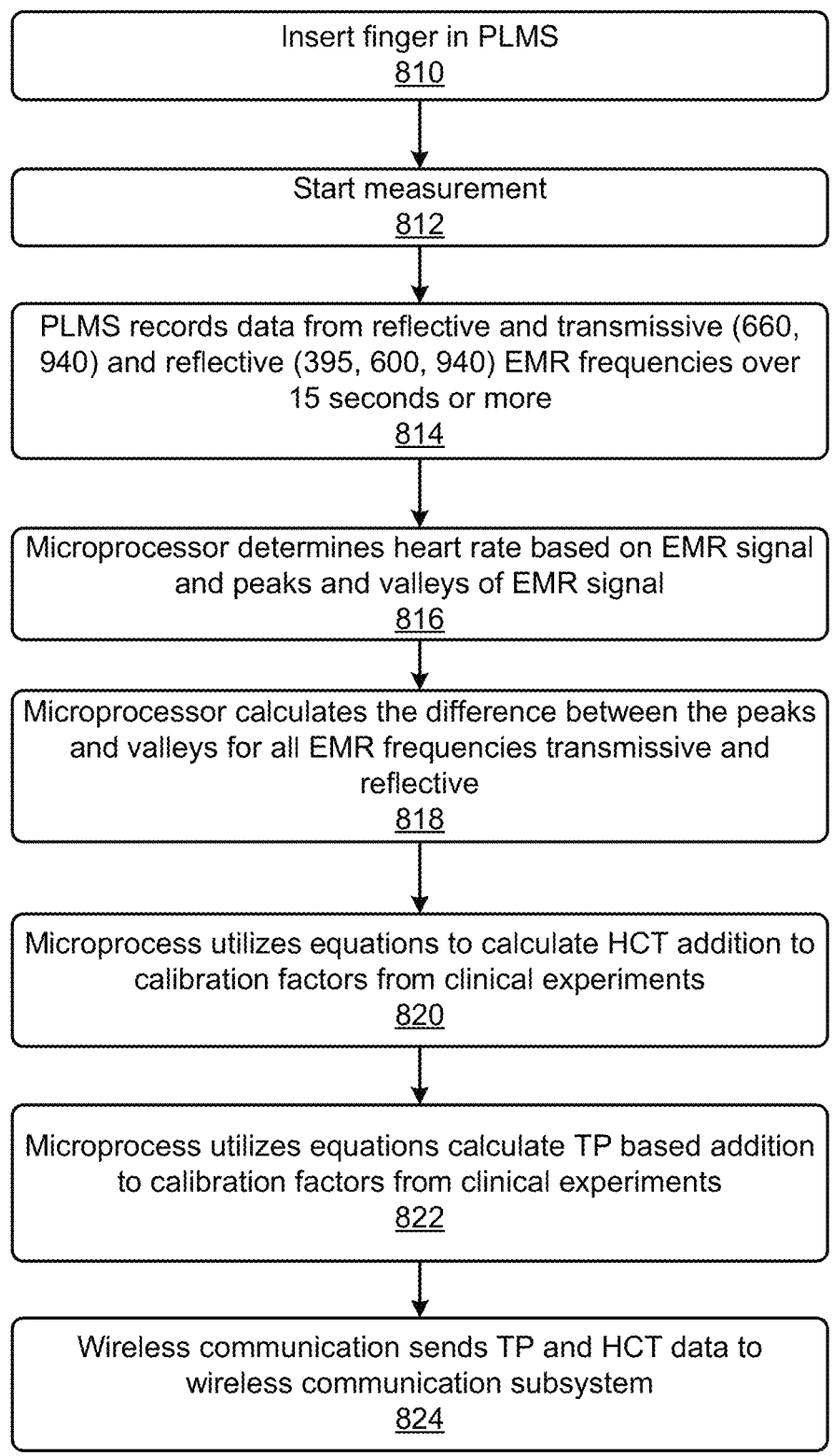
FIG. 20 illustrates a process flow for measuring Hc and TP.

FIG. 20 illustrates a process flow 800 for measuring Hc and TP employing the systems and methods described herein. After a finger has been inserted into the PLMS (810), measurements may begin (812) either automatically by way of finger detection using a proximity sensor, or via user initiation. Thereafter, the PLMS records transmissive and reflective data from the detectors for a period of 15 seconds or more ((814). The microprocessor determines heart rate (816) and calculates differences between peaks and valleys in the detected EMR data (818). The microprocessor then calculates Hc (820) and TP (822) and described above. The TP and Hc are then transmitted to a communications subsystem (824).

The VSMD's described herein may be equipped to communicate with a smartphone, via wired (USB port connection) or wireless (Bluetooth, WiFi, etc.) having an appropriate app installed thereon. Via the app, data can be uploaded from the VSMD to the smartphone for use by the app, and/or can be further uploaded to the RPMS. Via the app, firmware updates, feature upgrades, etc., to the VSMD may also be carried out.

Figure 21:
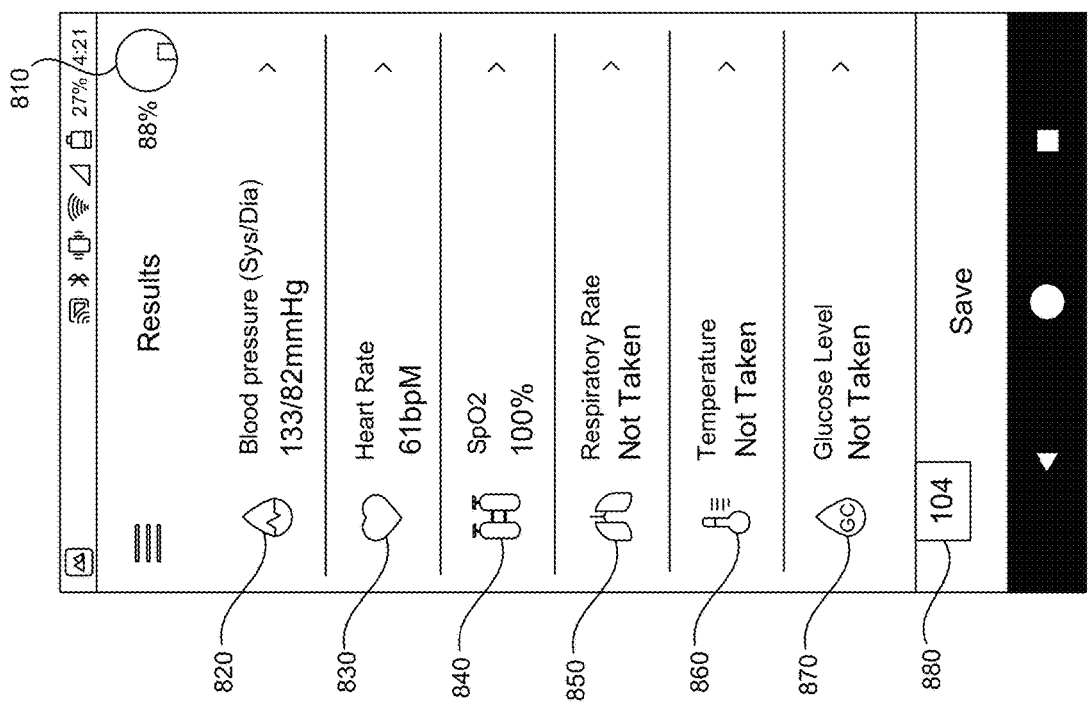
FIGS. 21-23 are displays of a smartphone running an app that shows result of vital sign measurements.

FIG. 21 illustrates a display of a smartphone running an app that shows result of vital sign measurements. The display includes display of the VSMD battery charge level (810), blood pressure (820), heart rate (830), SpO2 (840), respiratory rate (850), temperature (860), heart rate variability (870) and blood glucose level (880).

Figure 22:
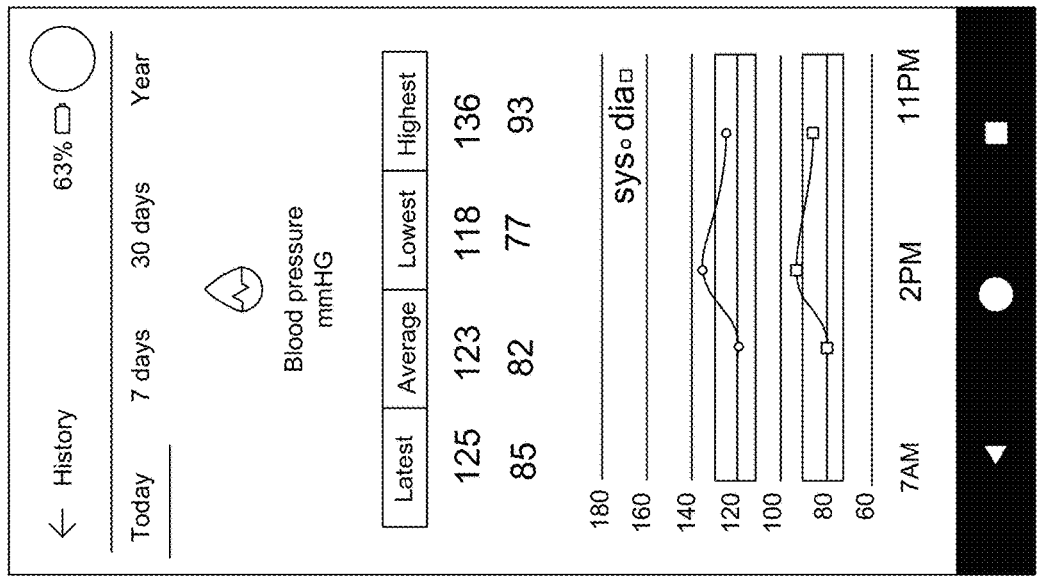

FIG. 22 is a display of the smartphone app showing a history of vital sign measurements.

Figure 23:
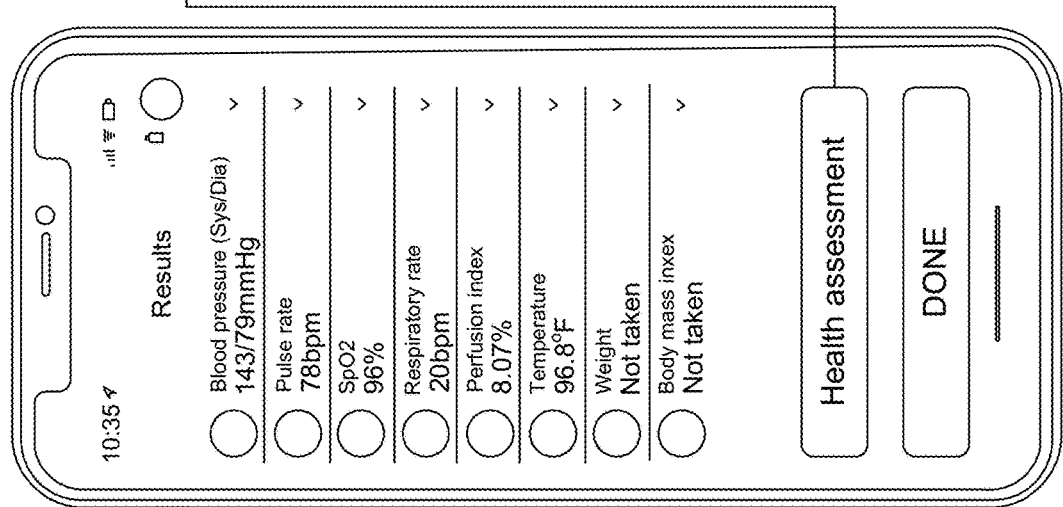

FIG. 23 is a display of the smartphone app screen showing the results of a recent vital sign measurement. The display may include a graphical user interface button ("health assessment") to display a screen of information on the health assessment from vital sign measurements, such as shown in FIG. 24.

Figure 25:
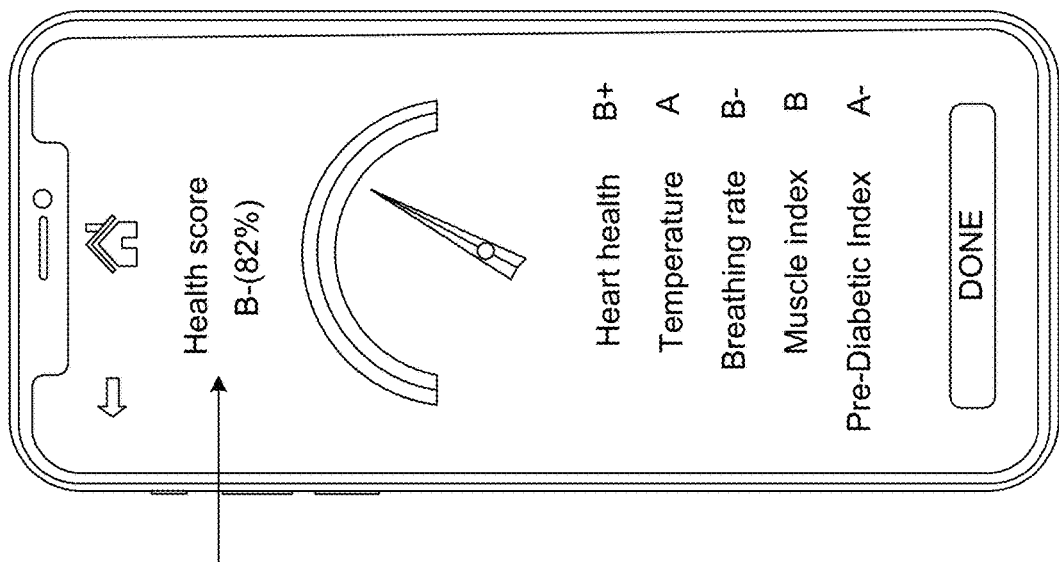
FIG. 25 is display of a smartphone running an app that shows health score.
Figure 24:
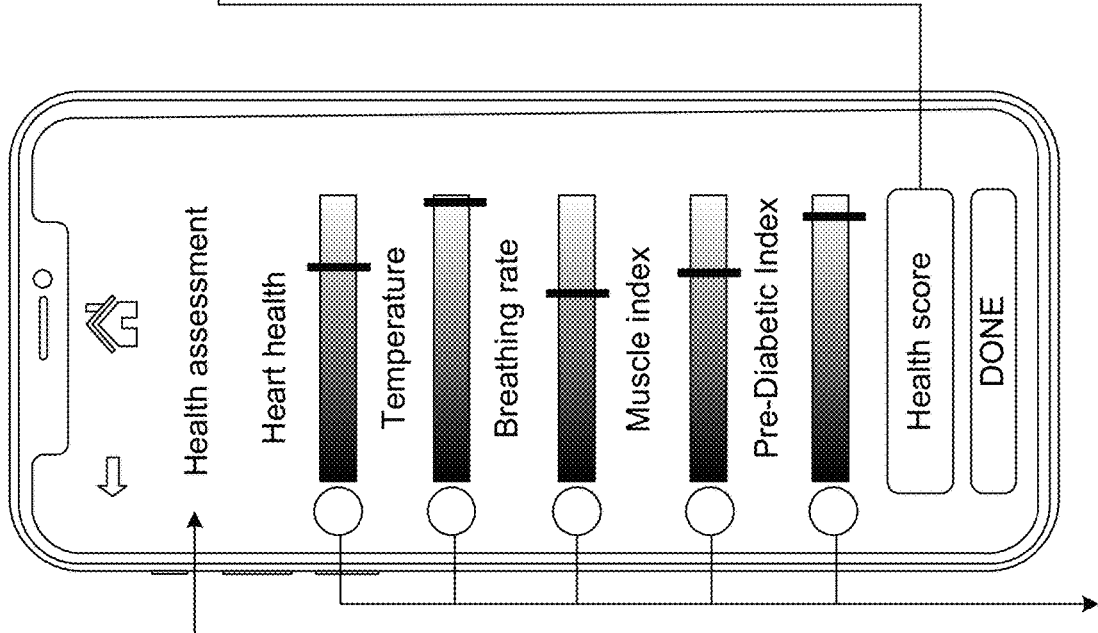
FIG. 24 is display of a smartphone running an app that shows health assessment.

The display of FIG. 24 includes a sliding scale graphical representation of heart health, temperature, breathing rate, muscle index and pre-diabetic index. The health assessment in FIG. 24 can be a subjective scale which illustrates the general well-being of a subject relative to the population norms or their own personal average baseline. The health assessment in FIG. 24 and the health score in FIG. 25 provide an interpretation of the vital sign measurements that illustrate the health information and health coaching that can be made possible. The display of FIG. 24 may include a graphical user interface button ("HealthScore") to display a screen of information on the health score from vital sign measurements.

The health score display of FIG. 25 includes a sliding scale graphical representation of overall health, a letter grade representation of heart health, temperature, breathing rate, muscle index, and pre-diabetic index. Detailed information on calculating a pre-diabetic index can be found in the References.

Figure 26:
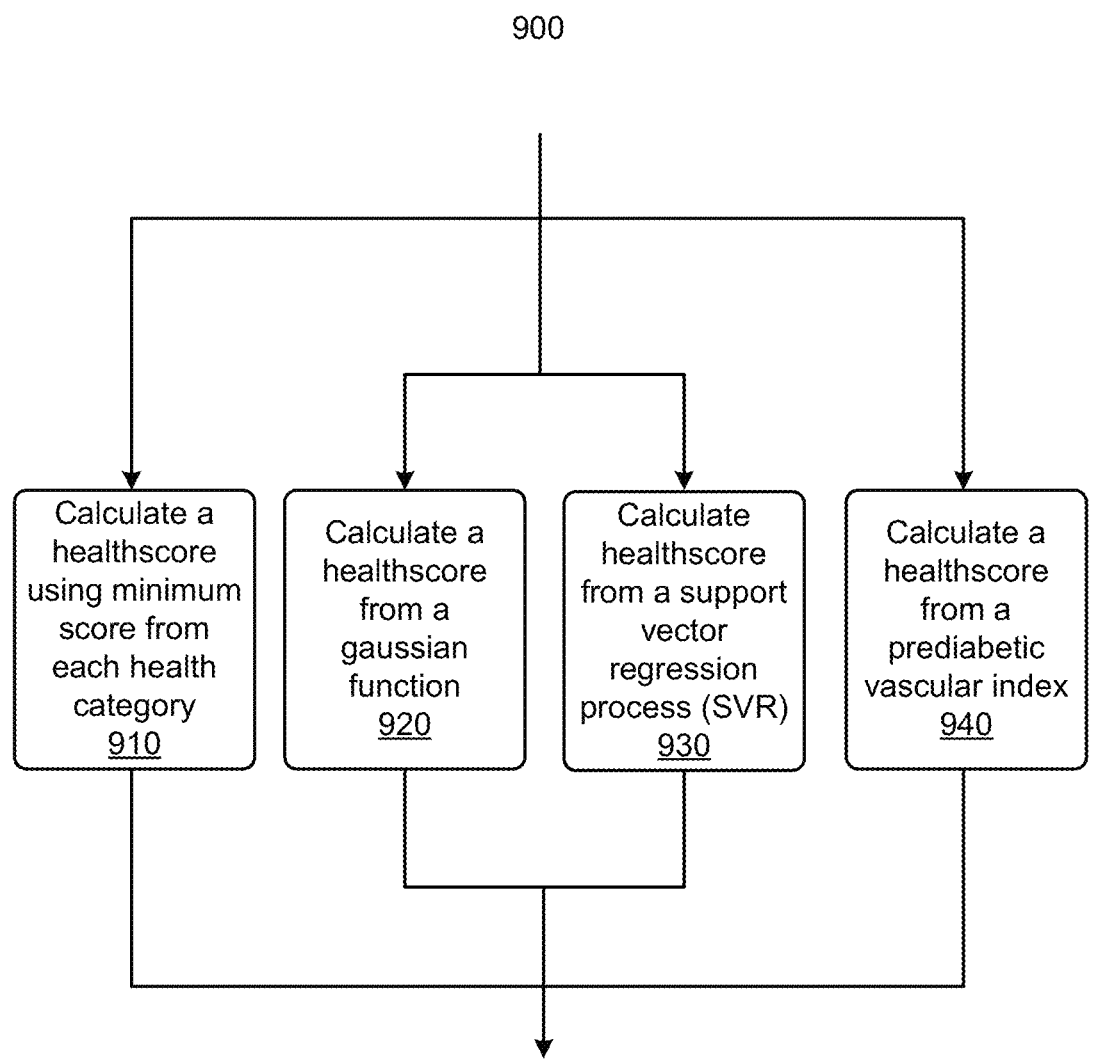
FIG. 26 illustrates a method of determining a health score from vital sign measurements.

FIG. 26 illustrates a method 900 of determining a health score from vital sign VS measurements. The health score may be calculated using the minimum score from each health category (e.g. heart health, lung health, temperature, body fat) (910), or from a Gaussian function (920) that can be used to represent a normal distribution for each vital sign as show below.

$$\text{health score for } i^{th} \text{ vital sign} = W_i e^{-\left(\frac{m_i - \mu_i}{c_i}\right)^2}$$

where
- $W_i$ is the respective weighting for the $i^{th}$ vital sign
- $m_i$ is the measured $i^{th}$ vital sign
- $\mu_i$ is the optimal $i^{th}$ vital sign
- $C_i$ is the Gaussian width factor for the $i^{th}$ vital sign Health scores may also be calculated using a vector support regression process (930). As mentioned, the health score may also include a pre-diabetic index (940).

The health score may be represented as a number (e.g. 0-10), a percentage (0-100%), or a grade letter (e.g. A, B, C). The scale for each health category can be based on numbers based on normal and abnormal ranges for the population (e.g. normal systolic is <120 mmHg, abnormal is >120 mmHg, normal temperature is between 97 and 99.5° F., abnormal temperature is >99.5° F.), or age based normal ranges, or even personal normal ranges establish by the average of previous time points.

The health score and health assessment can be integrated into a health wallet that captures the latest history (e.g. week/month) of vital sign measurements and integrates the latest history into a digital wallet of a smartphone. The health wallet can be a "pass" on the smartphone that contains a patient's latest vital signs and personal information and that can be accessed wirelessly. The health score and health assessment may be protected with a unique password or use the existing identification on the smartphone through biometrics such as fingerprints or face identification. The health wallet may be used as a digital health identification card that communicates via wireless communication to an EMIR or ambulance paramedic device.

Figure 27:
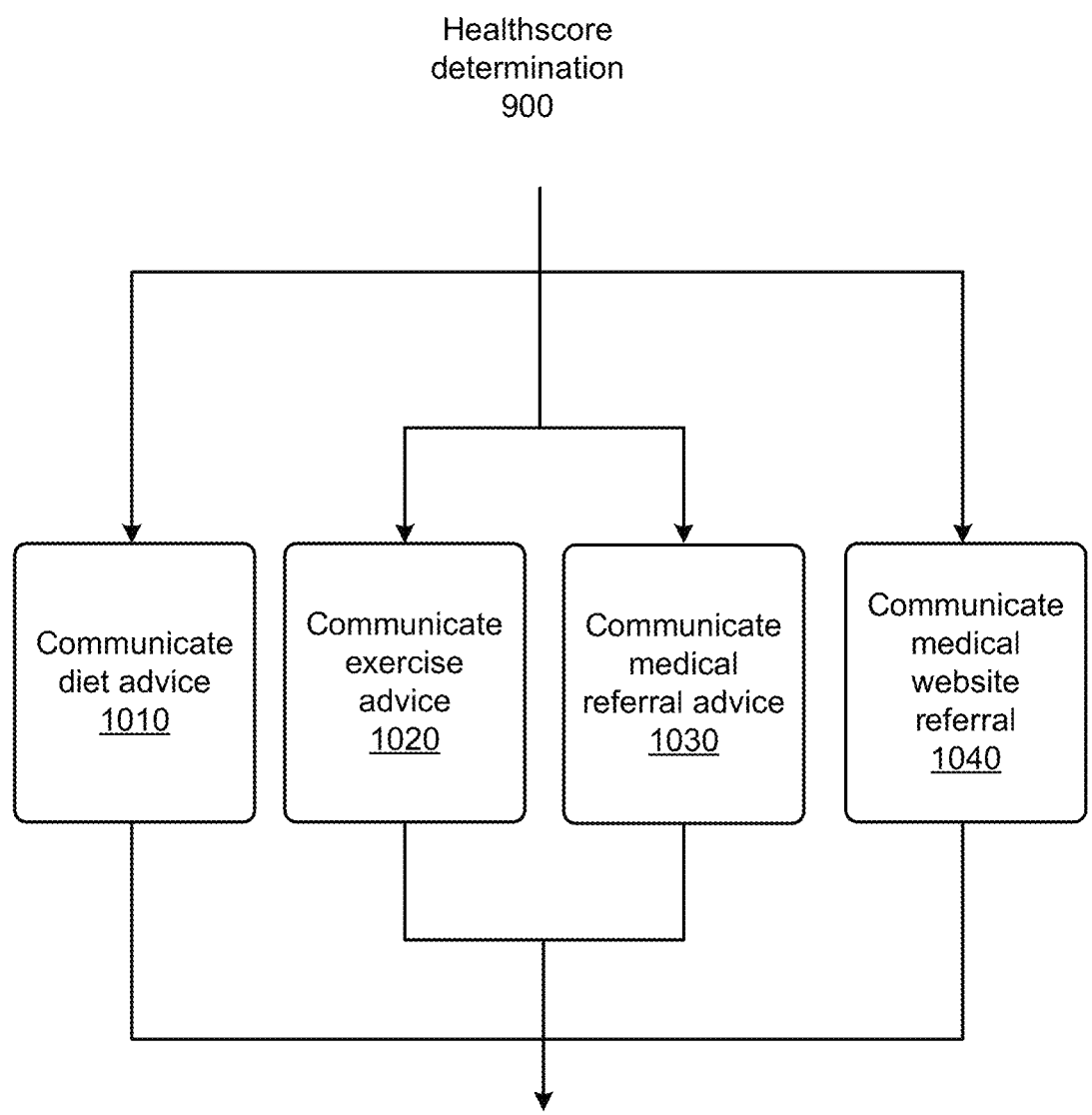
FIG. 27 illustrates a method of health coaching based on vital sign measurements with information on how to improve one's lifestyle.

FIG. 27 illustrates a method 1000 of health coaching based on vital sign measurements that conveys information on how to improve one's lifestyle. Health coaching may take the form of a person or an avatar that guides the user through methods to improve her health score and health assessment by identifying foods the user should be eating (1010) and what exercise she should be doing (1020). The health coach may advise the user to see a medical professional based on their vital signs through voice or text on the screen (1030). The health coaching may also link the user to useful information on the web (1040).

Figure 28:
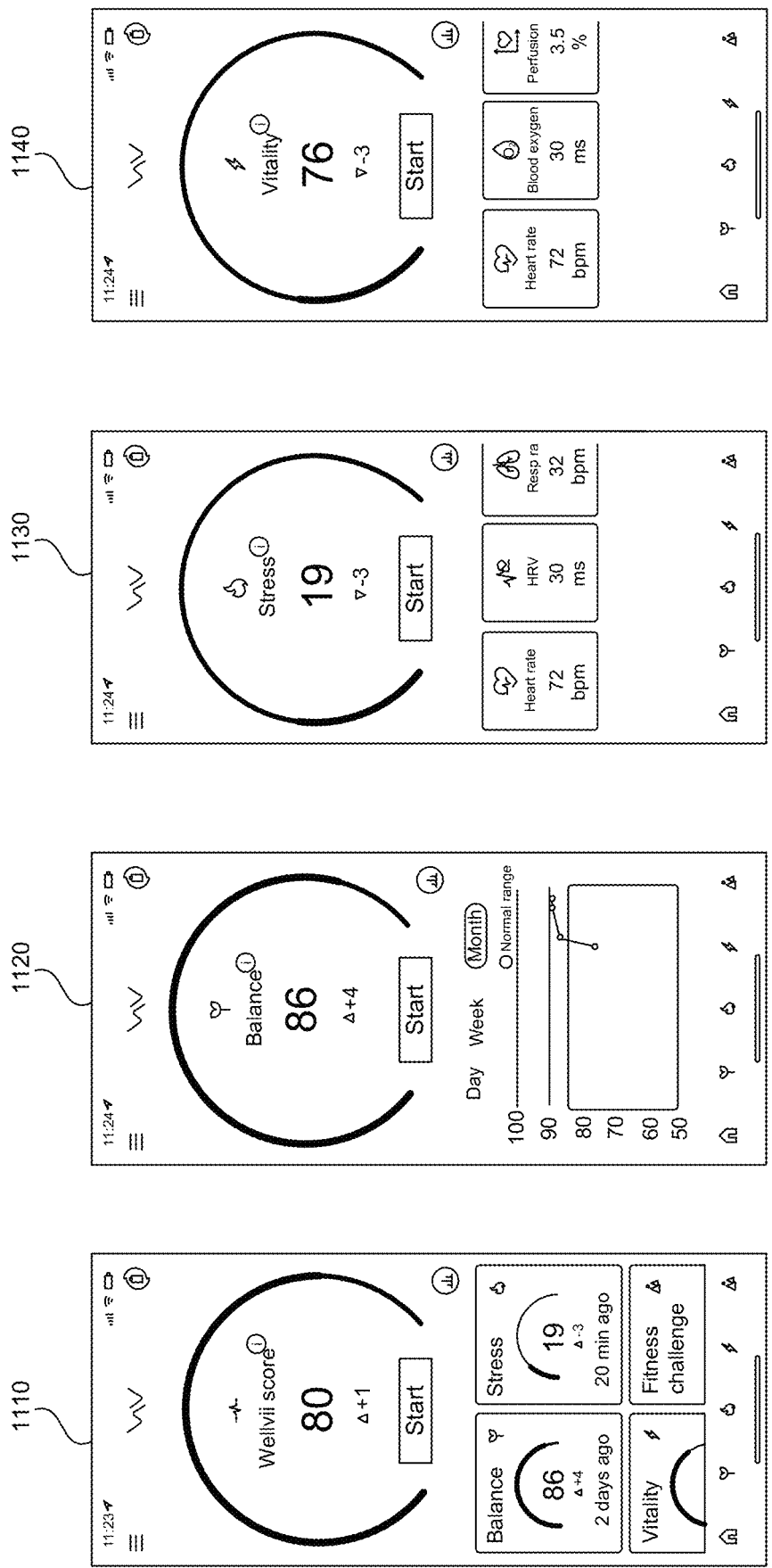
FIG. 28 illustrates exemplary displays on a smartphone running an app of health and wellness scores smart calculated from vital signs taken at different times of the day.

FIG. 28 illustrates an overall wellness score (1110) that may be calculated, based, for example, on a weighted average of a Balance (1120), Stress (1130), and Vitality (1140). The Balance score may be calculated from the standard deviation of the blood pressure, pulse pressure, heart rate, heart rate variability, blood oxygen, respiration rate, perfusion index, pleth variability index, and temperature and is take in the morning and evening when a person is at rest. The Stress score may be a measure of the change in a user's vital signs compared to those in the Balance state. The larger the change in the vital signs relative to the Balance State, the larger the Stress score. A Vitality score is calculated based on the microvascular flow and nitric oxide activity vital signs, where each vital sign is on a scale of 0-100. The further the vital signs are away from 100, the lower the score. A Gaussian penalty function may be applied.

FIG. 29 illustrates a fitness score (1210) based on one's vital signs before and after exercise or how well a person's vital signs recover after exercise. By measuring blood pressure, heart rate, heart rate variability, blood oxygen (SpO2), respiration rate before and after exercise, a score may be calculated on scale of 0-100. If the vital signs do not change, the persons score would be 100. The more elevated the vital signs compared to the measurement before exercise, the lower the score. Fitness challenges may be presented (122) and exercises recommended (1230).

Figure 30:
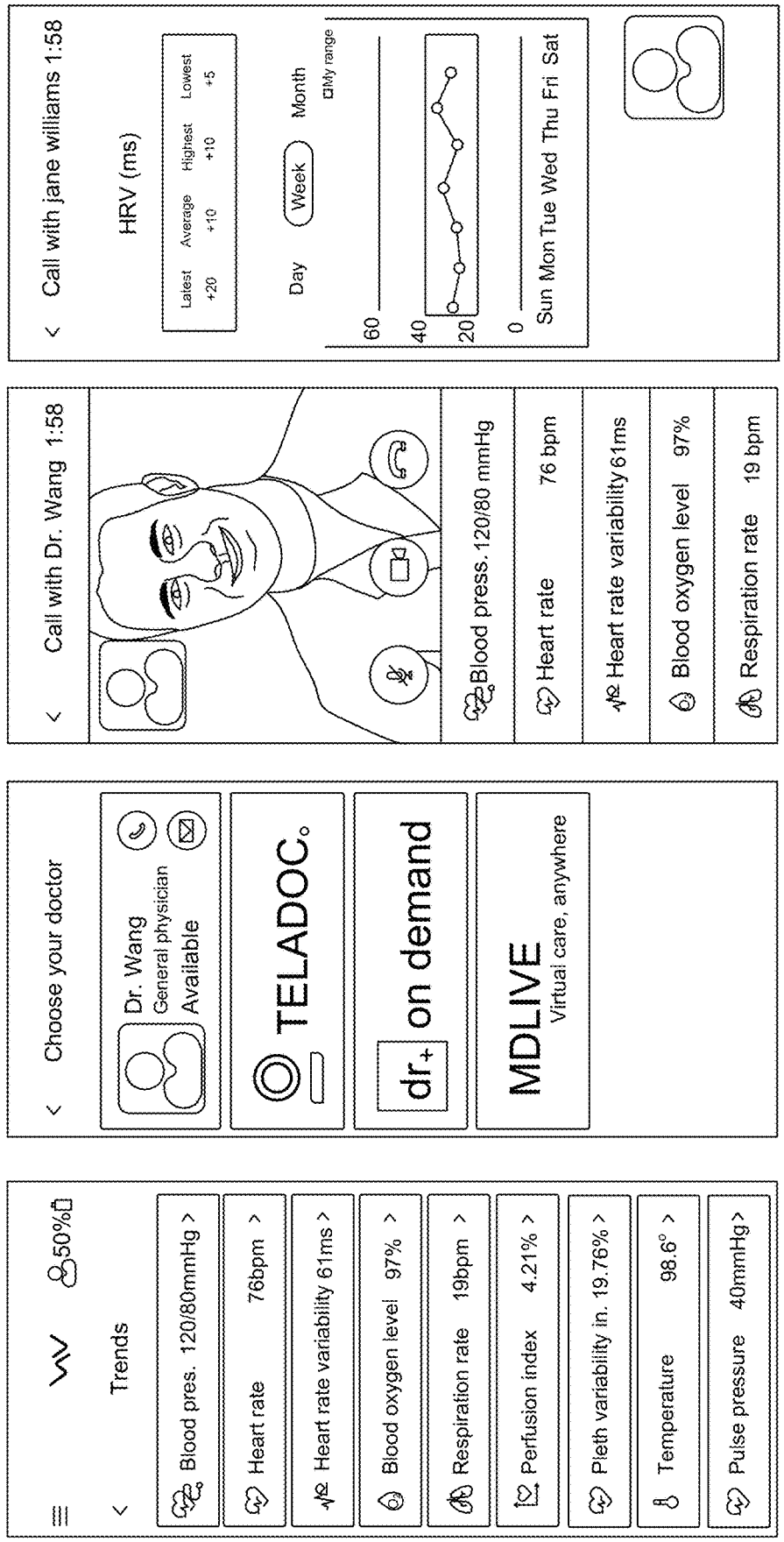
FIG. 30 illustrates exemplary displays on a smartphone running an app for a medical telehealth/telemedicine visit.

FIG. 30 illustrates exemplary displays on a smartphone running an app for a medical telehealth/telemedicine visit where the smart device application is integrated with different remote patient management systems (e.g. Teladoc, dr on Demand, and MDLive) to enable an audio/video conversation with the patient while vital signs measurements are being taken. The app in this case would simultaneously display the vital signs during the patient provider interaction.

The apparatuses, systems and methods described herein may be embodied in other specific forms without departing from the spirit or essential attributes thereof. Accordingly, reference should be made to the appended claims, rather than the foregoing specification, for indicating the scope of the innovations described herein.

What is claimed:

1. A vital sign measuring device (VSMD) adapted to non-invasively measure blood pressure (BP) and blood related characteristics of a person via a finger comprising:
   a) a base having a top and a bottom;
   b) discrete first and second axially aligned systems affixed to the top of the base so as to facilitate receipt of the finger, the bottom of the base being substantially flat and having an integral display for providing visual indications of BP and one or more of the blood characteristics, each system having a cavity adapted to receive a portion of a finger, the first system arranged to receive a proximal portion of the finger and the second system arranged to receive a distal portion of the finger, the first system adapted to measure only BP via the finger and the second system adapted measure only the blood related characteristics, including hematocrit (Hc) and total protein (TP),
   c) an inflatable bladder disposed in only the first system and adapted to envelope and apply pressure to only the proximal portion of the finger when inflated;
   d) a pump and a relief valve for inflating and deflating the bladder, respectively, a pressure sensor for providing data indicative of air pressure and air pressure oscillations in the bladder, a camera adapted to obtain images of a portion of the person's face, and a three - axis accelerometer for detecting movement of the VSMD, each of the pump, relief valve, pressure sensor, camera and accelerometer disposed in the base, and a stethoscope diaphragm disposed on the bottom of the base adapted to be held against the person's chest;
   e) a light emitting and light detecting system (PLMS) disposed in only the second system and comprising:
      i. an emitter only photodiode system disposed at an upper portion of the cavity of the second system and adapted to emit light onto a top portion of the finger adjacent a fingernail thereof at wavelengths of 660 nm and 940 nm; and, ii. an emitter and detector photodiode system disposed at a lower portion of the cavity of the second system and adapted to emit light onto a lower portion of the finger opposite the fingernail at wavelengths of 395 nm, 660 nm and 940 nm, receive 660 nm and 940 nm light emitted by the first photodiode system that has been transmitted through the finger, and receive 395 nm, 660 nm and 940 nm light emitted by the second photodiode system that has been reflected from the bottom portion of the finger;

f) there being no light emitter or detector systems employed to provide an indication of BP in either the first or second systems;

g) a control system disposed in the base and coupled to the first and second systems, the pump, the relief valve, the pressure sensor, the camera, the stethoscope diaphragm and the PLMS, including a microprocessor and a memory having program instructions for execution by the microprocessor stored therein for controlling the operation of the pump, the relief valve, the camera and the light emitting system, and for processing data received from the pressure sensor, the camera, the stethoscope diaphragm and the light detecting system by:

i) monitoring pressure data from the pressure sensor including an oscillometric pressure waveform detected in the pressure data;

ii) inflating the bladder to a predetermined pressure sufficient to occlude blood flow in portions of arteries of the finger inside the bladder;

iii) stopping bladder inflation when the predetermined pressure has been reached (inflation pressure) and thereafter controllably deflating the bladder;

iv) detecting resumption of blood flow in the arteries by monitoring the oscillometric pressure waveform;

v) detecting when normal flow has resumed by monitoring the oscillometric pressure waveform and detecting the pressure at which normal blood flow has resumed (deflation pressure);

vi)) calculating an indication of BP based on the oscillometric pressure waveform by generating a heart rate power spectrum from the waveform, then next convolving the power spectrum, and then next applying a fixed ratio method to provide an indication of systolic and diastolic BP;

vii) wherein none of steps g(1)—g(vi) employ data from a light emitter or a light detector;

viii) calculating indications of Hc and TP, and at least one of blood glucose level, respiration rate, saturation of peripheral oxygen, blood flow, total hemoglobin, pleth variability index, methemoglobin, acoustic respiration rate, carboxyhemoglobin, oxygen reserve index, oxygen content, nitric oxide, and microvascular blood flow, based on the amounts of reflected and transmitted light detected by the second photodiode system, wherein TP is calculated based upon the amount of detected 395 nm and 940 nm light reflected from the bottom portion of the finger as a result of light emitted by the second photodiode system and Hc is calculated based upon the amount of detected 660 nm and 940 nm light transmitted through the finger as a result of light emitted by the first photodiode system;

ix) cropping the images from the camera to exclude areas that do not include a skin region of the face and analyzing temporal motion of pixels of the cropped images to obtain indications of blood flow, heart rate, respiratory rate, BP, EKG, and blood oxygen (SpOz);

X) calculating a wellness score based on a combination of a balance score, a stress score and a vitality score, wherein: the balance score is calculated from a standard deviation in a combination of blood pressure, pulse pressure heart rate, heart rate variability, blood oxygen, respiration rate, perfusion index pleth variability index, and body temperature; the stress score is calculated as a measure of change in the person's vital signs compared to those in a reference state; and, the vitality score is calculated based on the indications of microvascular flow and nitric oxide;

xi) terminating the respiration rate measurement upon detecting movement via the accelerometer; and, xii) processing an output of the diaphragm to provide data indicative of heart beats;

h) the base, first and second systems, bladder, pump, relief valve, PLMS, camera, accelerometer, diaphragm and control systems being a single integral, self-contained, stand-alone unit.

\* \* \* \* \*